US009408405B2

(12) United States Patent
Gillessen et al.

(10) Patent No.: US 9,408,405 B2
(45) Date of Patent: Aug. 9, 2016

(54) USE OF COMPOUNDS THAT ARE ABLE TO INCREASE THE SERUM IGF-1 LEVEL FOR THE PREPARATION OF A THERAPEUTICAL COMPOSITION FOR TREATMENT OF VARIOUS DISEASE STATES ASSOCIATED WITH A REDUCED IGF-1 SERUM LEVEL IN HUMANS AND ANIMALS

(75) Inventors: Hubert Jean Marie François Gillessen, Lanaken (BE); Christian Rebiere, L'Herm (FR)

(73) Assignee: Veijlen N.V., Willemstad (CW)

( * ) Notice: Subject to any disclaimer, the term of this patent is extended or adjusted under 35 U.S.C. 154(b) by 1926 days.

(21) Appl. No.: 10/574,467

(22) PCT Filed: Oct. 3, 2003

(86) PCT No.: PCT/EP03/11171
§ 371 (c)(1),
(2), (4) Date: Oct. 11, 2007

(87) PCT Pub. No.: WO01/64205
PCT Pub. Date: Sep. 7, 2001

(65) Prior Publication Data
US 2008/0194553 A1    Aug. 14, 2008

(51) Int. Cl.
| | |
|---|---|
| A61K 31/405 | (2006.01) |
| A23K 1/16 | (2006.01) |
| A23K 1/165 | (2006.01) |
| A23K 1/18 | (2006.01) |
| A61K 31/404 | (2006.01) |
| A61K 31/4045 | (2006.01) |
| A61K 31/7056 | (2006.01) |
| C07D 209/18 | (2006.01) |

(52) U.S. Cl.
CPC .............. *A23K 1/1625* (2013.01); *A23K 1/165* (2013.01); *A23K 1/184* (2013.01); *A23K 1/188* (2013.01); *A23K 1/1826* (2013.01); *A23K 1/1893* (2013.01); *A61K 31/404* (2013.01); *A61K 31/405* (2013.01); *A61K 31/4045* (2013.01); *A61K 31/7056* (2013.01); *C07D 209/18* (2013.01)

(58) Field of Classification Search
CPC .......................... A61K 31/404; A61K 31/405
See application file for complete search history.

(56) References Cited

U.S. PATENT DOCUMENTS

| | | | |
|---|---|---|---|
| 3,689,657 A * | 9/1972 | Norman et al. ................ 514/382 |
| 4,025,650 A | 5/1977 | Gans et al. | |
| 4,650,789 A | 3/1987 | Pollack | |
| 4,687,763 A | 8/1987 | Wurtman | |
| 5,210,215 A | 5/1993 | Materazzi et al. | |
| 5,958,964 A | 9/1999 | Pappolla | |
| 6,017,946 A | 1/2000 | Posner | |
| 6,224,861 B1 * | 5/2001 | Abe et al. ................... 424/94.64 |
| 2002/0016354 A1 | 2/2002 | Teuber et al. | |
| 2002/0147155 A1 * | 10/2002 | Foster et al. ..................... 514/23 |
| 2002/0155163 A1 | 10/2002 | Benjamin et al. | |
| 2003/0166554 A1 * | 9/2003 | Cohen et al. ..................... 514/12 |

FOREIGN PATENT DOCUMENTS

| | | |
|---|---|---|
| CN | 1255349 A | 6/2000 |
| CN | 1408397 A | 4/2003 |
| CN | 1440744 A | 9/2003 |
| DE | 19739763 A | 9/1999 |
| DE | 10109798 A | 9/2002 |
| EP | 0482715 A | 4/1992 |
| EP | 0514373 A | 11/1992 |
| EP | 1064941 A | 1/2001 |
| FR | 2746313 A | 9/1997 |
| GB | 1475861 A | 6/1977 |
| GB | 1535778 A | 12/1978 |
| JP | 60-199801 | 10/1985 |
| JP | 7-025838 A | 1/1995 |
| JP | 8-98748 A | 8/1996 |
| JP | 8-198748 | 8/1996 |
| JP | 2002-281914 | 10/2002 |
| WO | WO 89/04659 A | 6/1989 |
| WO | WO 93/07870 A | 4/1993 |
| WO | WO 94/01121 A | 1/1994 |
| WO | WO 01/64205 | 9/2001 |
| WO | WO 01/64205 A | 9/2001 |
| WO | WO 02/080906 A | 10/2002 |

(Continued)

OTHER PUBLICATIONS

Patani et al 'Bioisosterism: A Rational Approach in Drug Design' Chemical Reviews, vol. 96, p. 3147-3176, 1996.*
Riley et al 'Aerobic work capacity in patients with chronic fatigue syndrome' British Medical Journal, vol. 301, p. 953-956, 1990.*
Lynch et al 'Antidepressant therapy in the chronic fatigue syndrome' British Journal of General Practice, vol. 41, p. 339-342, 1991.*
Nachshon-Kedmi et al. "Indole-3-carbinol and 3,3'-diindolylmethane induce apoptosis in human prostate cancer cells." Food and Chemical Toxicology vol. 41, No. 6, Jun. 2003 ISSN: 0278-6915.

(Continued)

*Primary Examiner* — Wu-Cheng Winston Shen
*Assistant Examiner* — Christopher R Stone
(74) *Attorney, Agent, or Firm* — TraskBritt, P.C.

(57) ABSTRACT

The present invention relates to the use of one or more compounds that are capable of increasing the serum level of insulin-like growth factor 1 (IGF-1) for the preparation of a therapeutical composition, in particular in the form of a food supplement, for the treatment of subjects suffering from serious fatigue and exhausting symptoms, burn-out and chronic fatigue syndrome. The same composition can also be used by patients suffering from depression, Alzheimer disease, irritated bowel syndrome, osteoporosis, type 2 diabetes, or for anti-aging, immune therapy and recovery after exercise. The composition also has a use in veterinary applications for increasing the growth and immunity in animals.

6 Claims, 11 Drawing Sheets

(56) References Cited

FOREIGN PATENT DOCUMENTS

Figure 1:
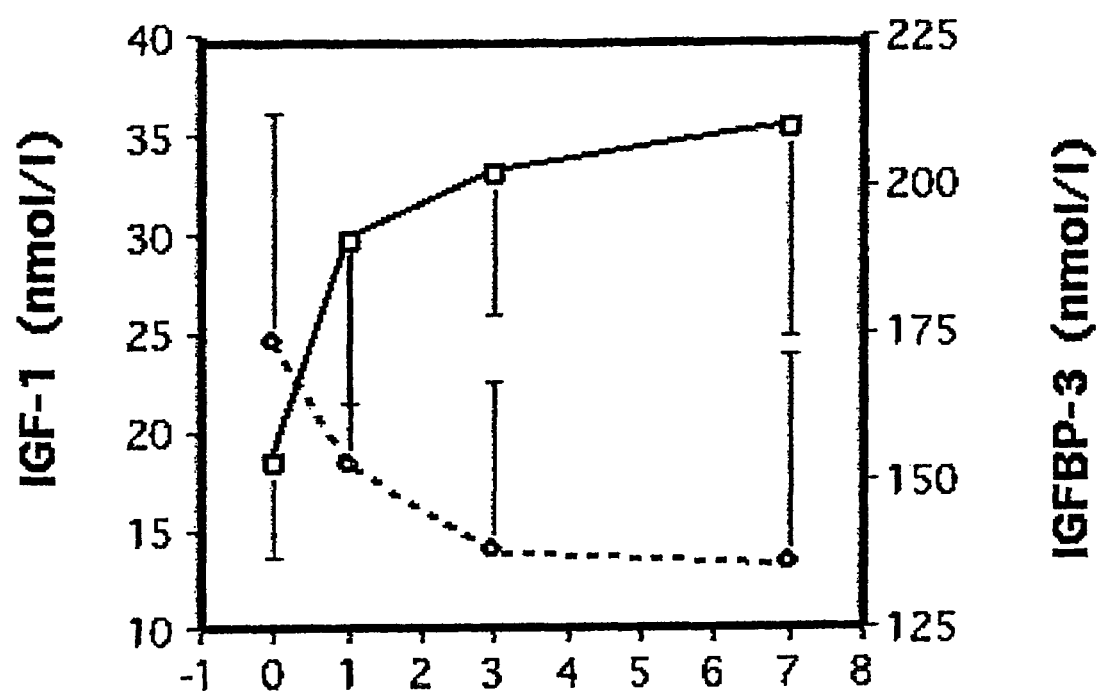

| WO | WO 03/080068 A | 10/2003 |
| WO | WO 2004/098498 | 11/2004 |

OTHER PUBLICATIONS

Rossiter, Sharon et al. "Halogenated indole-3-acetic acids as oxidatively activated prodrugs with potential for targeted cancer therapy" Bioorganic 7 Medicinal Chemistry Letters, 12(18), 2523-2526, 2002.

Folkes, Lisa et al. "5-Fluoroindole-3-acetic acid: a prodrug activated by a peroxidase with potential for use in targeted cancer therapy" Biochemical Pharmacology, 63(2), 265-272, 2002.

Fahey et al. "The chemical diversity and distribution of glucosinolates and isothiocyanates among plants" Phytochemistry, vol. 56, 2001, p. 5-51.

\* cited by examiner

USE OF COMPOUNDS THAT ARE ABLE TO INCREASE THE SERUM IGF-1 LEVEL FOR THE PREPARATION OF A THERAPEUTICAL COMPOSITION FOR TREATMENT OF VARIOUS DISEASE STATES ASSOCIATED WITH A REDUCED IGF-1 SERUM LEVEL IN HUMANS AND ANIMALS

The present invention relates to the use of one or more compounds that are capable of increasing the serum level of insulin-like growth factor 1 (IGF-1) for the preparation of a therapeutical composition, in particular in the form of a food supplement, for the treatment of subjects suffering from serious fatigue and exhausting symptoms, burn-out and chronic fatigue syndrome. The same composition can also be used by patients suffering from depression, Alzheimer disease, irritated bowel syndrome, osteoporosis, type 2 diabetes, or for anti-aging, immune therapy and recovery after exercise. The composition also has a use in veterinary applications for increasing the growth and immunity in animals.

Serious fatigue and exhausting symptoms occur as a result of a severe imbalance between the energy production on one side and an increased physical and/or psychological demand for energy on the other side.

Burn-out is defined as a gradual depletion of emotional, mental and physical energy due to work related stress leading to emotional exhaustion, a sense of depersonalization, and feelings of reduced personal accomplishment. Symptoms are poor work performance, relationship problems, health problems, negative feelings and feelings of meaninglessness.

Chronic fatigue syndrome (CFS) is defined as severe disabling fatigue which lasts at least 6 months, which is made worse by minimal physical or mental exertion, and for which there is no adequate medical explanation. Chronic Fatigue Syndrome has a feeling of fatigue (severe tiredness) as its main symptom. The fatigue should be new (i.e. not life-long), is severe, disabling, and affects the physical and mental function. It should persist for 6 months or more, and must be present 50% of the time. In addition, other symptoms may occur, especially myalgia (muscle aches), sore throat, swollen lymph nodes in the neck or armpits, pain without redness or swelling in a number of joints, intense or changing patterns of headaches, unrefreshing sleep and weariness that lasts for more than a day after any exertion. There is no other medical reason for fatigue (no heart problems, chest problems, or other medical problems which cause fatigue).

For these physical states no recognized treatments exist yet. Therefore, it is an object of the invention to provide a means to relieve at least some of the symptoms connected to these physical states.

It was found earlier that a subgroup of patients with CFS show depleted serum levels of insulin-like growth factor 1 (IGF-1). In order to increase the lowered IGF-1 serum levels IGF-1 is administered directly to an individual in need of treatment. However, the disadvantage thereof is that the IGF-1 concentration in the body may become too high in too short a time which might lead to an overdose. This in turn can cause hyperactivation (mitosis) which in the long run might lead to cancer.

Other conditions are also associated with reduced levels of IGF-1. It is also desirable to have treatments or reliefs for these.

It is therefore an object of the invention to provide an alternative means for increasing the IGF-1 serum level in an individual suffering from a condition in which a lowered IGF-1 serum level is found.

This is achieved according to the invention by the use of one or more compounds that are capable of activating the hypothalamus in an individual to increase the serum level of Growth Hormone Releasing Hormone (GHRH) which in turn leads to an increase in the secretion of growth hormone (GH) and the subsequent rise of the serum level of insulin-like growth factor 1 (IGF-1) for the preparation of a therapeutical composition for the treatment of serious fatigue and exhaustion symptoms, burn-out, chronic fatigue syndrome, irritated bowel syndrome, osteoporosis, depression, Alzheimer disease, type 2 diabetes, or for anti-aging therapy, immune therapy and for stimulating recovery after physical exercise.

It was found that the compound or compounds of the invention activate/stimulate the hypothalamus to an increased secretion of the growth hormone releasing hormone. This results in an increased release of growth hormone by the hypophysis. Actuated by insulin, the liver converts the growth hormone into the insulin-like growth factor 1 (IGF-1). The IGF-1 activates the tyrosine kinase receptors and the integrin receptors as a result of which inter alia the intracellular synthesis of lipid en glycogen will be stimulated and activated, which results in more energy. The compound that is used according to the invention also stimulates and activates the integrin receptors immediately, which activates and stimulates resistance/immunity.

Preferably, the compound is a compound that when administered to a human or animal individual to be treated can lead to an increased level of indole acetic acid (IAA) in the human or animal body in comparison to the level of indole acetic acid in the same human or animal body prior to administration of the compound.

The basic compound of the invention is thus indole acetic acid (IAA). However, the same result can be achieved by using derivatives and analogues of IAA or compounds that lead to an increased level of IAA. These derived compounds can therefore be divided into various categories.

In plants IAA is a major growth hormone. In its biosynthesis and further metabolism a number of compounds are known that are converted into IAA, either in the stomach, gut, liver or elsewhere in the body. This conversion can be enzymatical or chemical. In plants also a variety of hydroxylated, phosphorylated, methoxylated, N-oxides and N-methylated indole derivatives can be found. Thus the invention also relates to the use of compounds that can give IAA or IAA-derivative with similar activity, either directly or indirectly through metabolic conversion. These so-called precursors are for example 4-hydroxy-IAA, 4-methoxy-IAA, 5-hydroxy-IAA, 5-methoxy-IAA, 6-hydroxy-IAA, 6-methoxy-IAA, 7-hydroxy-IAA, 7-methoxy-IAA.

Furthermore the invention relates to the use of IAA with other substituents, compounds that may be either naturally occurring or synthetic. In nature halogenated indole alkaloids can be found, particularly in marine organisms (i.e. 6-bromoindigotin). Synthetically all types of substituents can be introduced on the aromatic ring, e.g. methyl, amino, nitro, fluoride, chloride, bromide, and iodide on the positions 4, 5, 6 and 7. This applies to all above mentioned natural occurring indole derivatives. Of these compounds all the above mentioned derivatives, conjugates and oxidation products can be formed. Either as synthetic products or as the result of metabolism by living cells (plants, microorganisms, mammalian cells, human body).

The invention also relates to the use of precursors from which IAA and analogues as listed above could be formed, such as tryptophan, 4-hydroxytryptophan, 4-methoxytryptophan, 5-hydroxytryptophan, 5-methoxytryptophan, 6-hydroxytryptophan, 6-methoxytryptophan, 7-hydroxytryptophan 7-methoxytryptophan, hypaphorine, tryptamine, 4-hydroxytryptamine, 4-methoxytryptamine, psilocin (4-hydroxy, dimethyl tryptamine), psilocybin (4-phosphate, dimethyl tryptamine), baeocystin, serotonin (5hydroxytryptamine), 5-methoxytryptamine, bufotenine (dimethylserotonine), O-methylbufotenine, melatonin (5-methoxy, acetamide function on tryptamine $NH_2$), 6-hydroxytryptamine, 6-methoxytryptamine, 7-hydroxytryptamine, 7-methoxytryptamine.

Other naturally occurring precursors for IAA formation are indole butyric acid and indole-3-pyruvate.

The invention further relates to the use of compounds that are analogues or metabolites from IAA that may be converted back into IAA (or related derivatives as mentioned above) or have a similar activity. For all these compounds also the above mentioned 4-, 5-, 6- and 7-hydroxy- and methoxy-derivatives are claimed. These compounds are for example indole, indole-3-acetaldehyde, indole-3-ethanol, indole-3-aldehyde, indole-3-methanol, indole-3-carboxylic acid, 3-methylindole (skatole), indole-3-acetaldoxime, 3-aminomethylindole, N-methylaminomethylindole, Gramine (N-dimethylaminomethylindole). Similar compounds are compounds with changed indole chromophore, such as indoxyls (indicans), indoleninones, 3-methylene-2-oxindole, abrine, isotan B, isatin, indican, indigo, indurubin, indigotins 3-indolylmethyl (skatolyl), niacin, 2-oxindole-3-acetic acid Another group are the IAA-metabolites, that are commonly found in plants, such as 3-methylene-2-oxindole, oxindole-3-methanol, oxindole-3-aldehyde, oxindole-3-carboxylic acid, 3-methyloxindole.

For all naturally occurring indole compounds (see above) a series of simple derivatives and conjugates is found in nature. These compounds are also suitable for the use of the invention. Such derivatives are N-oxides both for N1 and (if present) the aliphatic amino group, N1-acetyl-, N1-formyl-, N1-O-methyl, N1-methyl or N1-sulfate derivatives of all mentioned indole derivatives and the oxidation products having a 3-hydroxyindolenine function.

Furthermore, the invention relates to the use of conjugates of IAA or IAA analogues with different other molecules abundant in plants, such as conjugates via an ester bond, in particular with various sugars, for example IAA-glucose, IAA-alfa-aspartic acid 1N-glucoside, IAA-inositol, IAA-myoinositols, IAA-various carbohydrates or conjugates as amides for example with amino acids and peptides. Example thereof are acetamide, alfa-leucine, alfa-alanine, alfa-aspartate (most important conjugate of IAA), alfa-glutamate, alfa-lysine, alfa-glycine, alfa-valine and alfa-phenylalanine. Conjugation with peptides is common, whereas also conjugates with other amino acids occur in different plants. In addition, this group comprises 3-acetonitrile derivatives, which easily are converted into the corresponding acid, like indole-3-acetonitrile that decomposes in IAA both chemically (under basic conditions) and catalytically (by nitrilases).

Another category of compounds that can lead to an increase in IAA are enzymes that lead to the liberation of IAA from other compounds or to the conversion of precursor compounds into IAA. IAA is liberated from the amides by amidases (amidohydrolysases). IAA and related compounds are released from the glucosides by glucosidases. In plants considerable amounts of conjugated IAA can be present, which can be liberated either by enzymatic (e.g. glucosidases or amidases) or chemical hydrolysis. Of the total IAA pool, amide linked IAA constitutes 90%, whereas 10% is ester linked and 1% is free IAA. In plants, the levels of free+bound IAA are about 1.2 ug/g Dry Weight (for *Arabidopsis* 9 days old, later lower). Of this only 1% is free IAA.

Furthermore, the invention relates to the use of conjugates (esters and amides) of other natural IAA derivatives such as 2-oxindole derivatives and 4-, 5-, 6- or 7-hydroxyderivatives: dioxindole-3-acetic acid (and conjugates as for IAA), 3-O-beta-glucosyl-dioxindole-3-acetic acid 7-hydroxy-2-oxindole-3-acetic acid-7'-O-beta-d-glucopyranoside, glucopyrasonyl-beta-1,4-glucopyranosyl-beta-1-N-oxindole-3-acetyl-N-aspartic acid, glucopyranosyl-beta-1-N-oxindole-3-acetyl-N-aspartic acid, 2-indolone-3-acetyl aspartic acid, 3-(O-beta-glucosyl)-2-indolone-3-acetyl aspartic acid, 3-hydroxy-2-indolone-3-acetyl aspartic acid indole-3-glycerophosphate (decomposes in IAA under basic conditions), indole-3-glycerol (decomposes in IAA under basic conditions), glucosinolates, such as indole-3-ylmethyl glucosinolate (glucobrassicin), 4-hydroxyindol-3-ylmethyl glucosinolate (4-hydroxyglucobrassicin), 1-acetyl-indol-3-ylmethyl glucosinolate (1-acetyl-glucobrassicin), 1-methoxyindol-3-ylmethyl glucosinolate (neoglucobrassicin), 4-methoxyindol-3-ylmethyl glucosinolate (4-methoxyglucobrassicin), 1-sulfo-indol-3-ylmethyl (glucobrassicin-1-sulfate) which are converted into indole derivatives by myrosinases (thioglucosidases).

The invention is useful for the treatment of patients showing various indications that are associated with a lowered serum level of IGF-1. IGF-1 mediates largely the anabolic action of growth hormone. It stimulates the uptake of glucose and amino acids, the protein synthesis and cell proliferation, and leads to an increased nitrogen balance. In addition, IGF-1 inhibits apoptosis.

It was found that for the various indications there are optimal amounts of IAA to be administered. In addition, for some indications the eating pattern may be important.

For chronic fatigue syndrome (CFS) the amount of the compound that is used for treatment is such that it leads to an equivalent activity of a daily intake of 40 mg IAA. In a preferred embodiment 40 mg of IAA is administered each day. The amount may be reduced over a period of 2 to 4 weeks depending on the serum concentration of IGF-1 and IGF-BP3. For example, when the ratio IGF-BP3/IGF-1 decreases the amount of IAA administered may be reduced. For this indication the subject to be treated should take in sufficient carbohydrates and lipids. However, this can be achieved by a normal eating pattern, i.e. no low-fat, sugar-free or low-carbohydrate diet.

The same eating pattern applies to the treatment of burn-out, but the starting amount of the compound that is used for treatment is such that it leads to an equivalent activity of a daily intake of 20 mg IAA. In a preferred embodiment 20 mg of IAA is administered each day.

For anti-aging the eating pattern is not important. The amount of the compound that is used for treatment is such that it leads to an equivalent activity of a daily intake of 4 mg IAA. In a preferred embodiment 4 mg of IAA is administered each day during several months depending on the individual.

For each of these indications it is preferred to do light exercise to further stimulate the hypothalamus.

When the composition of the invention is used as a food supplement for individuals that perform heavy exercise, such as racing cyclists or marathon runners additional fats and/or carbohydrates are needed. These individuals usually start with a normal IGF-1 serum level and the level decreases during exercise. The metabolism is higher and additional nutrients are needed. The starting amount of the compound that is used for supplementation is such that it leads to an equivalent activity of a daily intake of 40 mg IAA. In a preferred embodiment 40 mg of IAA is administered each day during 2 weeks and after that depending on the level of training 90 to 30, 20, 10, 4 mg.

The use of the invention can also lead to an improvement in the immunity of humans and animals. Regulation of immunity by IGF-1 mainly takes place on the autocrine and paracrine level between immunocompetent cells in the bone marrow, secondary lymphoid organs and peripheral tissues. IGF-1 regulates haematopoiesis and direct effector function of cells of the innate as well as the acquired immune system. IGF-1 works through the integrin receptor that is found on cells of the cellular immune systems, such as lymphocytes. The production of interleukins and tumor necrosis factor (TNF) is increased. Through this mechanism IGF-1 can have a beneficial effect on infections, inflammation, allergies, rheuma etc.

Furthermore, it was found that the IGF-1 levels in serum of type 2 diabetes patients is reduced. The invention can thus also be used in the treatment of these patients.

The composition of the invention is preferably in the form of a capsule, but other dosage forms, preferably oral dosage forms, such as tablets, oral suspensions, oral emulsions, oral fluids, powders, lozenges, pastilles, pills, etc., are also possible. The composition may for example take the form of a food supplement or a pharmaceutical composition.

The utility of the invention in the treatment of the indicated indications is based on experimental data that are set out in the Examples. In summary these results show the following.

Eight patients suffering from severe chronic fatigue syndrome (CFS), were studied during 5-7 months. In this period they were treated with a therapeutical composition of the invention in the form of a food supplement, which comprised IAA as the active ingredient. All subjects were unable to do their job or to perform very light physical exercise.

Before entering the study, the subjects underwent a careful medical examination to exclude any other disease. Blood was assayed for insulin-like growth factor 1 (IGF-1) and its major binding protein IGF-BP3 was sampled at 0, 1, 3 and 5-7 months of treatment because the total amount of IGF-1 in serum minus the amount of IGF-BP3 is the amount of free IGF-1. Free IGF-1 is the active serum fraction. Also at 0, 1, 3 and 5-7 months job participation and physical activities were registered and calculated as percentage of normal, before disease pattern.

Before treatment job participation was 6.2%, and physical activity was only 16.3% of normal. Treatment with the composition of the invention increased job participation already after 1 month to 16.2%, which increased further to about 69.4% after 5 months. Also the ability for muscular exercise was significantly increased after 1 month of treatment, and was almost 100% after 5 months of treatment.

Plasma IGF-1 levels increased significantly from 18±5 nmol/l (mean ±SD) to 29.5±8.2 nmol/l after 1 month. After 5 months of treatment IGF-1 was further increased to 35±10 nmol/l. IGF-BP3 decreased from 25±11.5 nmol/l to 18.1±3.5 and 13.4±10.6 nmol/l after 1 and 5 months of treatment, respectively. This means that the biologically active fraction of IGF-1 was increased. This thus showed that IAA can be used for modulating the growth hormone status in CFS patients.

An experiment with 4 patients suffering from type 2 diabetes showed that the patients felt better upon treatment with the composition of the invention. The same applied to individuals with general aging problems in whom the composition of the invention gave an improvement on all symptoms.

The recovery of racing cyclists and trialists after heavy exercise is improved after treatment with a food supplement of the invention.

In animal experiments it was shown that the weight of poor growing animals treated with IAA increased to normal levels. These experiments are illustrative of the fact that the compounds used according to the invention lead to an increased appetite and a better stimulation of the integrin receptors, which in turn leads to a better immunity and therefore a lower risk of infections and consequently less use of antibiotics.

The utility of the invention can also be derived from literature that shows that the insulin-like growth factor 1 (IGF-1) is involved in various indications. The composition of the invention leads to an increase in IGF-1 serum levels and is therefore suitable for treatment of conditions in which the IGF-1 levels are decreased. In the following relevant publications are listed that further support the utility of the invention for treatment of various indications.

The utility for the treatment of osteoporosis is based on the following literature references: "Endocrine causes of age-related bone loss and osteoporosis", Riggs B. L., *Novartis Found. Symp* 242 (2002): 247-259; "Serum insulin like growth factor I, bone mineral density and biochemical markers of bone metabolism in children with idiopathic osteoporosis", Chlebna-Sokol D., Rusinka A., *Endocr. Regul.* 35 (2001): 201-208; "Effects of growth hormone and insuline like growth factor I on body growth and adult bone metabolism", Ohlsson C., Jansson Jo, Isaksson O., *Curr. Opin. Rheumatol.* 12 (2000): 346-348; "Comparison of serum insulin-like growth factor-I and growth hormone levels in osteoporotic and non osteoporotic postmenopausal women", Celiker R., Arslan S., *Rheumatol. Int.* 19 (2000): 205-208; "Does macular hole formation have a hormonal cause?", *Klin. Oczna.* 102 (2000): 191-193; "Low serum IgF-I and occurence of osteo porotic fractures in post menopausal women", Gamero P., Somay-Rendu E., Delmas P. D., *The Lancet* 355 (2000): 9207; "Effects on growth hormone on phosphocalcium homeostasis and bone metabolism", Saggese G., Baroncelli G. I., Federico G., Bertelloni S., *Horm. Res.* 94 suppl. 3 (1995): 55-63; "Growth hormone (GH) and adult bone remodeling: the potential use of GH in treatment of osteoporosis", Brixen K., Kassem M., Eriksen E. F., Nielsen H. K., Flyvbjerg A., Mosekilo L., *J. Pediatr. Endocrinol.* 6 (1993): 65-71.

The use of the invention for treatment of inflammatory bowel disease follows from the following references: "Chronic inflammation and the effect of IgF-1 on muscle strength and power in older persons", Barbieri M., Ferrucci L., Rogno E., Corsi A., Bandinelli A., Bonafe M., Olivieri F., Giovagnetti S., Franceschi C., Guralnik J. M., Paolisso G., *Am. J. Physiol. Endocinol. Metab.* 284 (2003): E 481.1.; "Reduces serum insulin-like growth factor I (IgF-1) and IgF binding protein-3 levels in adults with inflammatory bowel disease", Katsanos K. H., Tsatsoulis A., Christdoulon D., Challa A., Katsaraki A., Tsianos E. V., *Growth Horm. IgF Res.* 11 (2001): 364-367; "Insulin-like growth factor-1 (IgF-1) and growth hormone (GH) in immunity and inflammation", Heemskerk V. H., Daemen M. A., Buurman W. A., *Cytokine Growth Factor Rev.* 10 (1999): 5-14.

Stimulation of immunity by means of the invention is based on the following literature: "Cytokine profile of rheumatoid module suggests that it is: The I granuloma", Hersian P. A., Highton J., Kean A., Sun C. K., Chin M., *Arthritis Rheum.* 48 (2003): 334-338; "Newly available treatments for psoriatic arthritis and their impact on skin psoriasis", Galadari H., Fuchs B., Lebwohl M., *Int. J. Dermatol.* 42 (2003): 231-237; "Anti TNF-alpha therapy for rheumatoid arthritis; an update", Taylor P. C., *Intern Med.* 42 (2003): 15-20; "IgF-1 inhibits spontaneous apoptosis in human granulocytes", Kooijman R., Coppens A., Hooghe-Peters E., *Endocrinology* 143

(2002): 1206-1212; "Tissue-specific regulation of IgF-I and IgF-binding proteins in response to TNF-X", Charles H. Lang, Gerald J. Nystrom, and Robert A. Frost, *Growth Hormone & IgF Research* 11 (2001): 250-260; "The roles of Prolactin, Growth Hormone, Insuline-like Growth Factor-I and Thyroid Hormones in lymphocyte development and function: insights from genetic models of hormone and hormone receptor deficiency", Kenneth Dorshkid and Nelson D. Horseman, *Endocrine Reviews* 21 (2000): 292-312; "The Thymus and the acute phase response", Haeryfar S. M., Bercri, *Cell. Mol. Biol.* 47 (2001): 145-146; "Prolactin, growth hormone and the immune system in humans", Velkeniers B., Doguson Z., Naessens F., Hooghe R., Hooghe-Peters E. L., *Cell Mod. Life Sci.* 54 (1998): 1102-1108; "Effects of growth hormone and insuline-like growth factor I binding to natural killer cells", Bidlingmaier M., Auernhammer C. J., Feldmeier H., Strasburger C. J., *Acta Paediatr. Suppl.* 423 (1997): 80-81; "The somatogenic hormones and Insulin-like growth Factor I: stimulators of lymphopoiesis and immune function, Ross Clark, *Endocrine Reviews* 18 (1997): 157-179; "The immune effects of neuro peptides", Berezi I., Chalmers I. M., Nagy E., Warrington R. J., *Baillieres Chin. Rheumatol.* 10 (1996): 227-257; "Effects of growth hormone and Insuline-like growth factor I on the immune system", Auernhammer C. J., Strasburger C. J., *Eur. J. Endocrinol.* 133 (1995): 635-645.

The utility of the invention for the treatment of depression and Alzheimer disease is based on the following references: "Initiation factor 2B activity is regulated by protein phosphatase 1, which is activated by the mitogen-activated kinase (MAPK)-dependent pathway in insulin like growth factor 1-stimulated neuronal cells, Quevedo C., Salinas M., Alcazar A., *J. Biol. Chem.* 6 (2002): 638-639; "Adenoviral gene transfer of GDNF, BDNF and TGF beta 2, but not CNTF cardiotrophin-I or IgF-I, protects injured adult motoneurons after facial nerve avulsion", Sakamoto I., Kawazoey, Shen J. S., Takeday, Arakawa Y., Ogawa I., Oyanagi K., Ohashi I., Watanabek, Inoueh, Eto Y., Watabe K., *J. Neurosci. Res.* 72 (2003): 54-64; "Serum insulin-like growth factor I regulates brain amyloid beta levels", Caro E., Trejo J. L., Gomer-Isla T., Le Roith D., Torres-Aleman I., *Nat. Med.* 8 (2002): 1390-1397; "Circulating Insuline-like Growth factor I mediates the protective effects of physical exercise against brain insults of different etiology and anatomy", Carro E., Trejo J. L., Busiguina S., Torres-Aleman I., *J. Neurosci.* 21 (2001): 5678-5684; "Estrogen augments glucose transporter and IgF-1 expression in primate cerebral cortex", Cheng C. M., Cohen M., Wang J., Bondy C. A., *Faseb. J.* 15 (2001):907-915; "Insulin like growth factor I induced survival of axotomized olfactory neurons in the chick", Mathonnet M., Comti I., Lallone F., Ayer-le Lievvre C., *Neuosci. lett.* 308 (2001): 3: 67-70; "Insulin-like growth factor I regulates developing brain glucose metabolism", Cheng C. M., Reinhardt R. R., Lee W. H., Joncas G., Patel S. C., Bondy C. A., *Proc. Natl. Acad. Sci.* USA 29, 97 (2000): 10236-10246.

The anti-aging effect of the composition of the invention is based on the following literature: "Models of growth hormone and IgF-1 deficiency: application to studies of aging processes and life-span determination", Carter C. S., Ramsey M. M., Ingram R. L., Coshion A. B., Cefaki W. T., Wang Z. Q., Sonntag W. E., *J. Gerontol. A. Bid. Sci. Med. Sci.* 57 (2002): B177-188; "Effects of growth hormone and insuline-like growth factor I deficiency on ageing and longevity", Laron Z., *Novartis Found. Symp.* 242 (2002): 125-137; "Growth hormone, somatomedins and men's health", Beckers A. J., Uckert S., Stief C. G., Jonas U., *Aging Male* 5 (2002): 258-262; "Growth hormone in the elderly man", Reid M., Kotzmann H., Luger A., *Wien. Med. Wochenschr.* 151 (2001): 426-429; "Growth hormone, insuline-like growth factor I and cognitive function in adults", Van Dam P. S., Aleman A., de Vries W. R., Deijen J. B., van der Veen E. V., de Haan E. H., Koppeschaar H. P., *Growth Horm. IgF Res.* 10 suppl. B (2000): S69-73; "Growth hormone and insulin like growth factor I as anabolic agents", Weel S., *Curr. Opin. Chin. Nutr. Metab. Care* 1 (1998): 257-262; "Growth hormone secretion in the elderly; ageing and the somatopause", Martin F. C., YEO AL., Sonksen P. H., *Baillieres Chin. Endocrinol. Metab.* 11 (1997): 223-250; "Fuel metabolism in growth hormone deficient adults", Jorgensen J. O., Moller N., Wolthers T., Moller J., Grofte T., Vahl N., Fisker S., Orskov H., Christiansen J. S., *Metabolism* 44 (1995): 103-107; "Human growth hormone and human aging", Corpas E., Harman S. M., Blackman M. R., *Endocr. Rev.* 14 (1993): 20-39; "Aging and anti-aging effects of hormones", Everitt A., Meites J., *J. Gerontol.* 44 (1989): B139-147.

The use of the invention for the treatment of type 2 diabetes can be derived from the following references: "Association between the insulin resistance of puberty and the insuline-like growth factor I/growth hormone axis", Moran A., Jacobs D. R., Steinberger J., Cohen P., Hong C. P., Prineas I., Sinaiko A. R., *J. Chin. Endocrinol. Metab.* 87 (2002): 4817-4820; "IgF-I/IgF binding protein-3 combination improves insulin resistance by GH dependent and independent mechanisms", O. Connell T., Celmmons D. R., *J. Chin. Endocrinol. Metab.* 87 (2002): 4356-4360; "Defective insuline secretion in pancreatic beta cells lacking type I IgF receptor", Xuan S., Kitamura T., Nakae J., Politi K., Kido Y., Fisher P. E., Morroni M., Cinti S., White M. F., Herrera P. L., Accili D., Efstratiadis A., *J. Clin. Invest.* 110 (2002): 1011-1019; "Structure and autoregulation of the insuline-like growth factor I receptor kinase",. Favelyukis S., Till J. H., Hubbard S. R., Millar W. *T., Nat. Struct. Biol.* 8 (2001): 1058-1063; "Distinct and overlapping functions of insulin and IgF-1 receptors", Nakae J., Kido Y., Accili D., *Endocr. Rev.* 22 (2001): 818-835; "Glucose effects on skin keratinocytes: implications for diabetes skin complications", Sprachikov N., Sizyakov G., Gartsbein M., Accili D., Tennenbaum T., Wertheimer E., *Diabetes* 50 (2001): 1627-1635; "Lack of insulin like growth factor I (IgF-I ) in the basal keratinocyte layer of diabetic skin and diabetic foot ulcers", Blakytny R., Jude E. B., Martin Gibson J., Boulton A. J., Ferguson M. W., *J. Pathol.* 90 AO (2000): 589-594; "Current status and future prospects of parenteral insulin regimens, stategies and delivery systems for diabetes treatment", Jeandidier N., Boivin S., *Adv. Drug Deliv. Rev.* 35 (1999): 179-198.

The composition of the invention is furthermore useful for stimulating muscles, such as the heart muscle, as can be derived from the following literature: "Regulation of insulin-like growth factor I in skeletal muscle and muscle cells", Frost R. A., Lang C. H., *Minerva Endocrinol.* 28 (2003): 53-73; "Cardiac specific IgF-1 expression attenuates dilated cardiomyopathy in tropomodulin-overexpressing transgenic mice", Wlech S., Plank D., Witt S., Glascock B., Schaefer E., Chimentis, Andreoli A. M., Limana F., Ceri A., Kajstura J., Anversa P., Sussman M., *Circ. Res.* 95 (2002): 90: 641-648; "IgF-I activates PKC alpha-dependant protein synthesis in adult rat cardiomyocytes", Pecherskaya A., Solem M., Moll. *Cell. Biol. Res. Commun.* 4 (2000): 166-171; "Insulin like growth factor-I receptor and its lig and regulate the reentry of adult ventricular myocytes into the cell cycle", Reiss K., Cheng W., Pierchalski P., Kodali S., Li B., Wang S., Liu Y., Anversa P., *Exp. Cell Res.* 235 (1997): 198-209; "Overexpression of insulin-like growth factor I in mice protect from myocyte death after infarction, attennocting ventricular dilation, wall stress, and cardiac hypertropphy", Li Q., Li B., Wang X., Leri A., Jana K. P., Liu Y., Kajstura J., Baserga R., Anversa P., *J. Clin. Invest.* 100 (1997): 1991-1999; "Myo cardial infarction and the myocyte IgF-I autocrine system", Anversa P., Reiss K., Kajstura J., Cheng W., Li P., Sonneblick E. H., Olivetti G., *Eur. Heart J.* 16 suppl. (1995): 37-45; "Upregulation of IgF I, IgFI-receptor, and late growth related genes in ventricular myocytes acutely after infaction in rats", Reiss K., Meggs L. G., Li P., Olivetti G., Capasso J. M., Anversa P., *J. Cell Physiol.* 158 (1994): 160-168.

The present invention will be further illustrated in the following examples that are not intended to limit the invention. Reference is made to the following figures:

FIG. 1: The course of plasma IGF-1 and IGF-BP3 level in time in 8 patients, suffering from CFS. The patients were treated with the food supplement of the invention.

Figure 2:
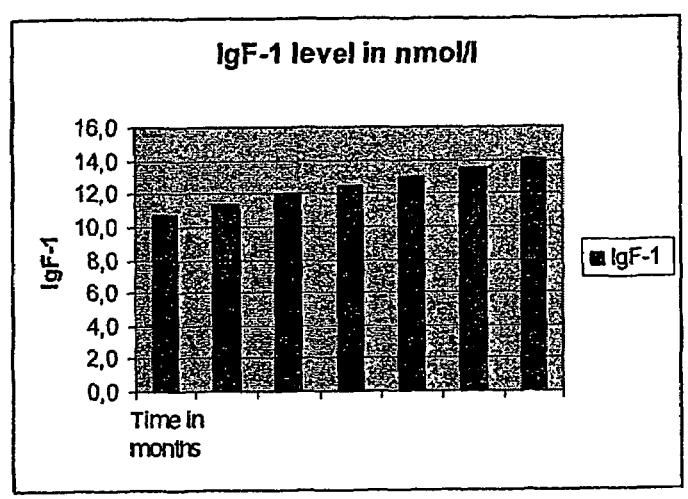

FIG. 2: IGF-1 levels in nmol/l in type 2 diabetic patients during medication with IAA.

Figure 3:
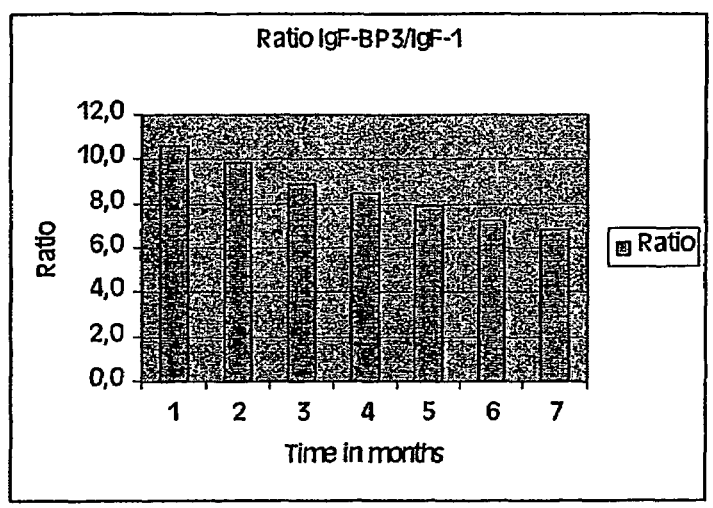

FIG. 3: The ratio of IGF-BP3/IGF-1 in type 2 diabetic patients during medication with IAA.

Figure 4:
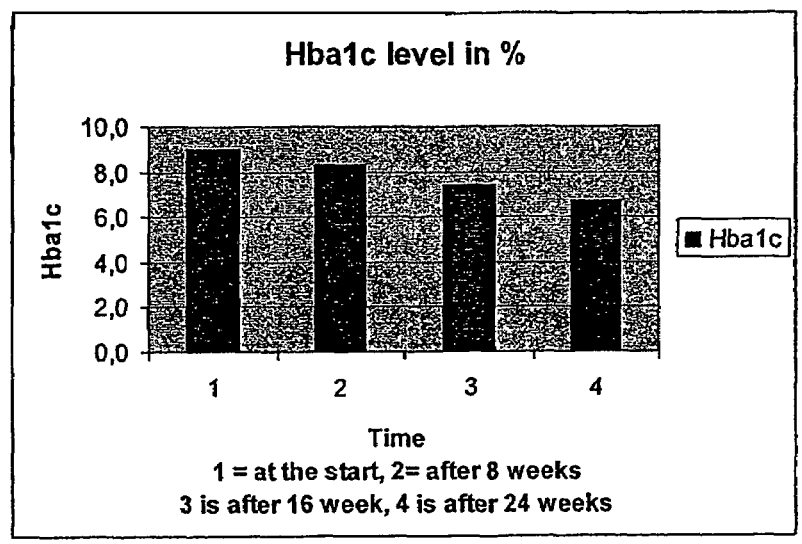

FIG. 4: The HbAlc (hemoglobin Alc) level in type 2 diabetic patients during medication with IAA.

Figure 5A:
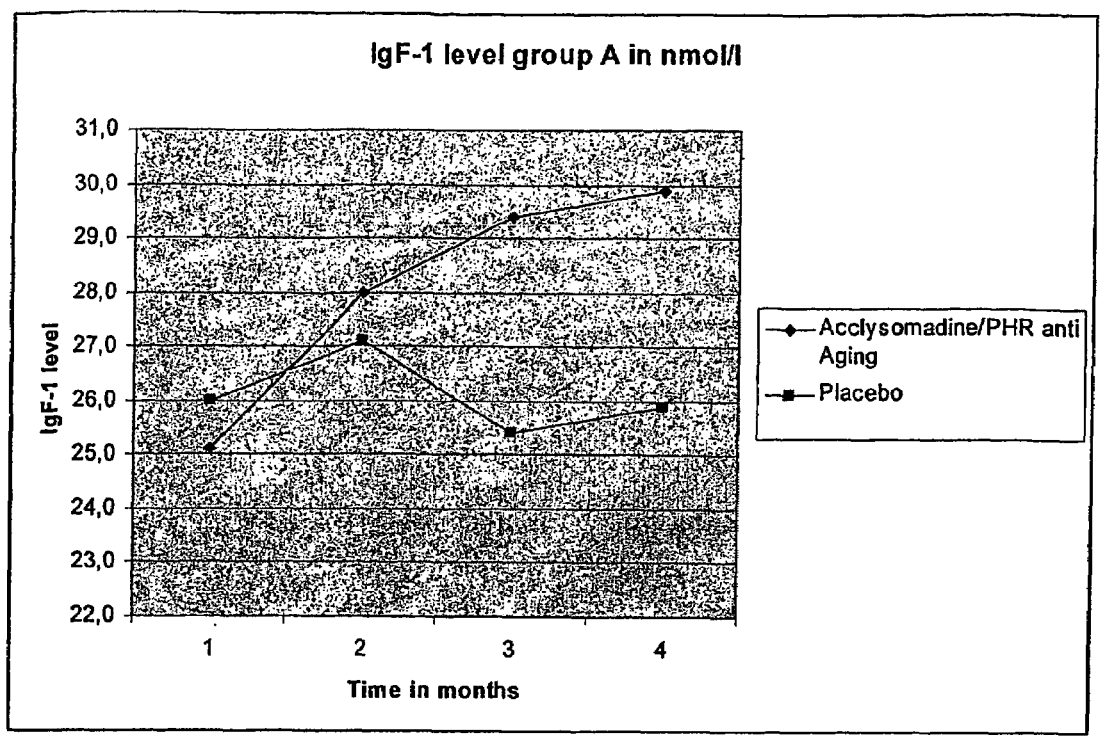
Figure 5B:
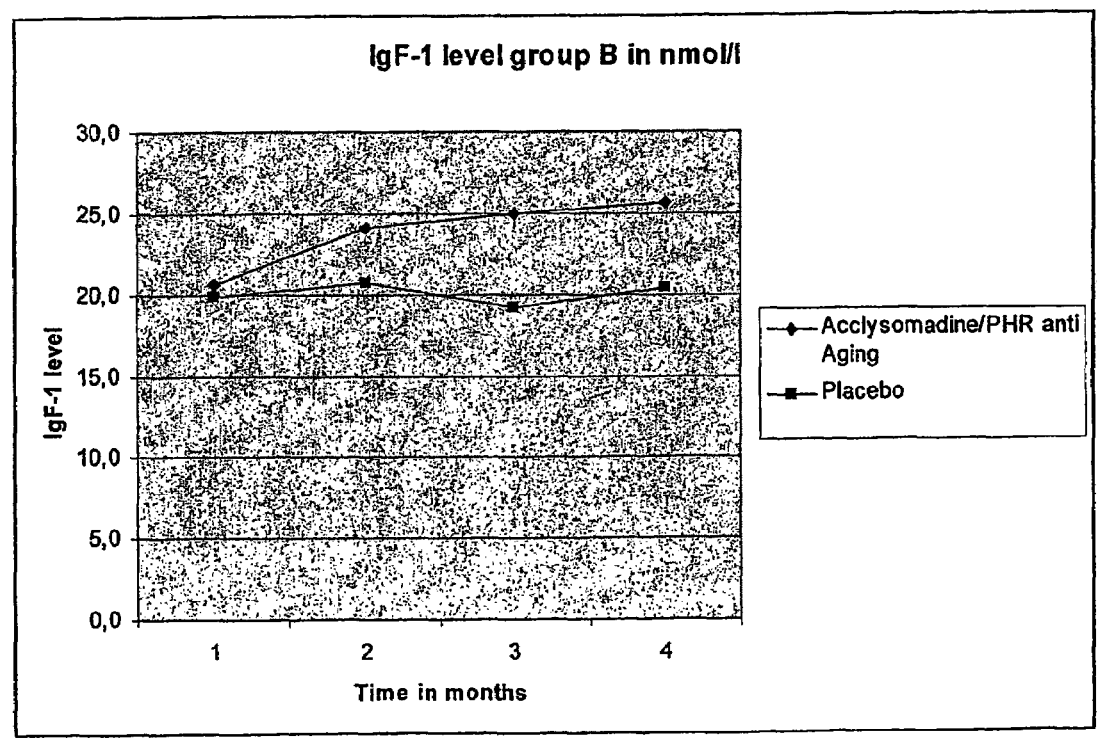
Figure 5C:
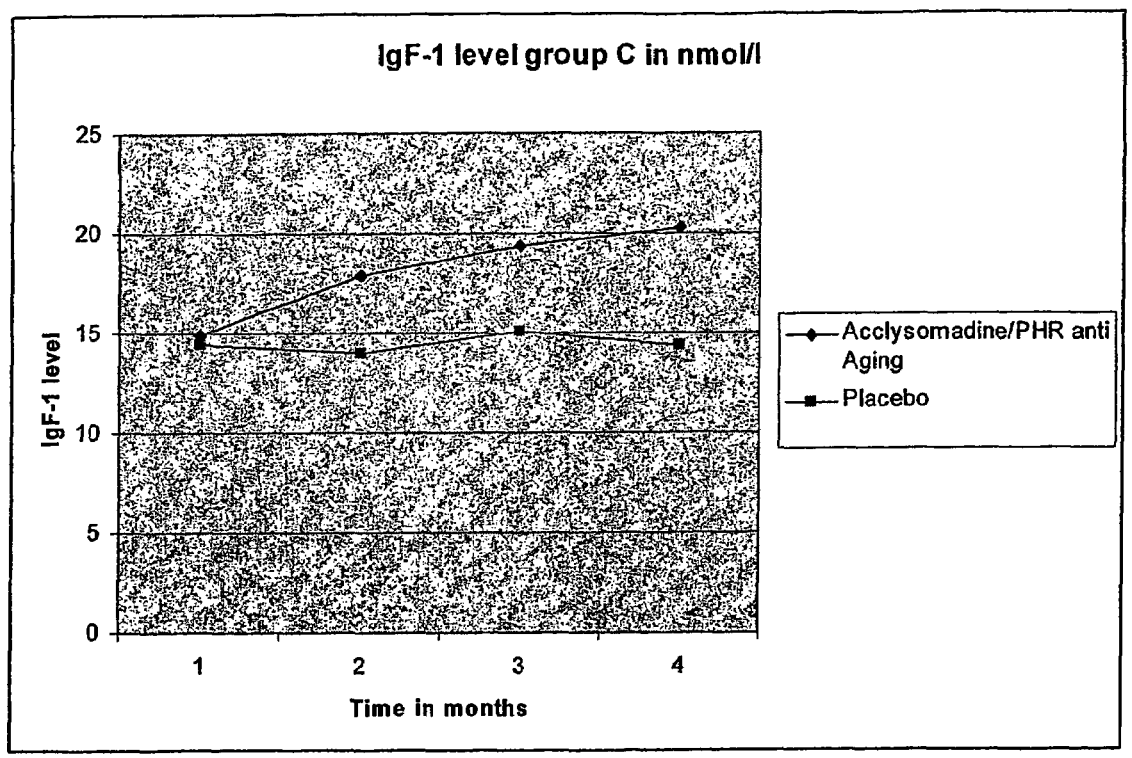

FIG. 5A-C: IGF-1 levels in individuals with general anti-aging problems during medication with a composition of the invention.

Figure 6A:
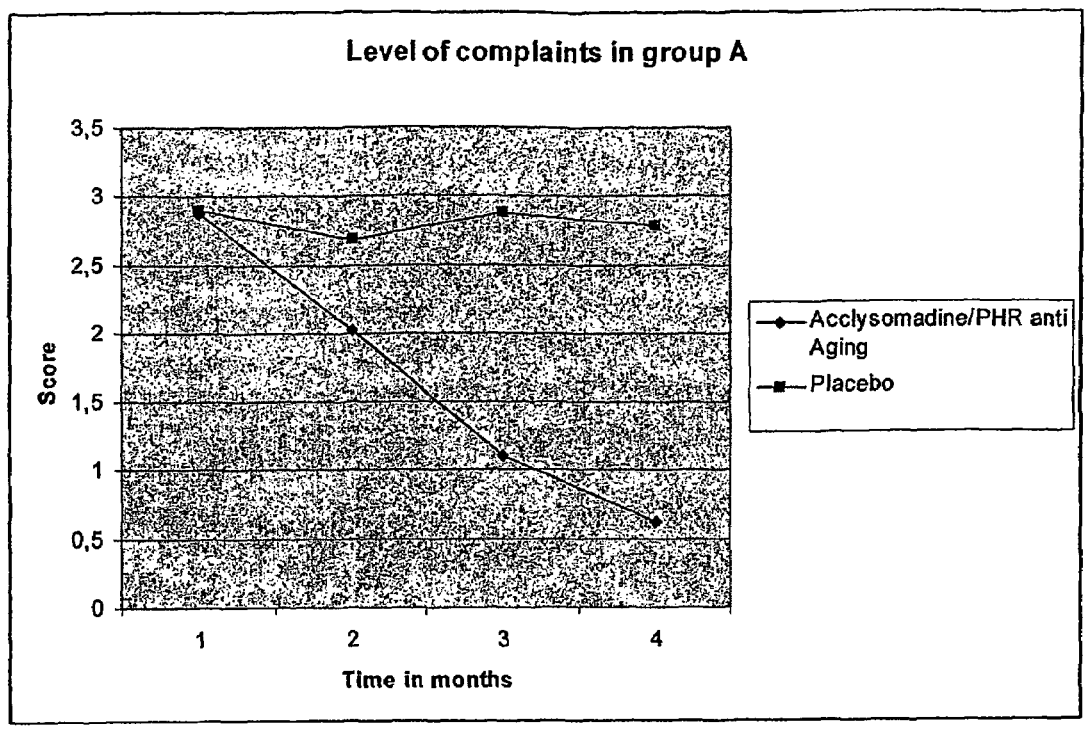
Figure 6B:
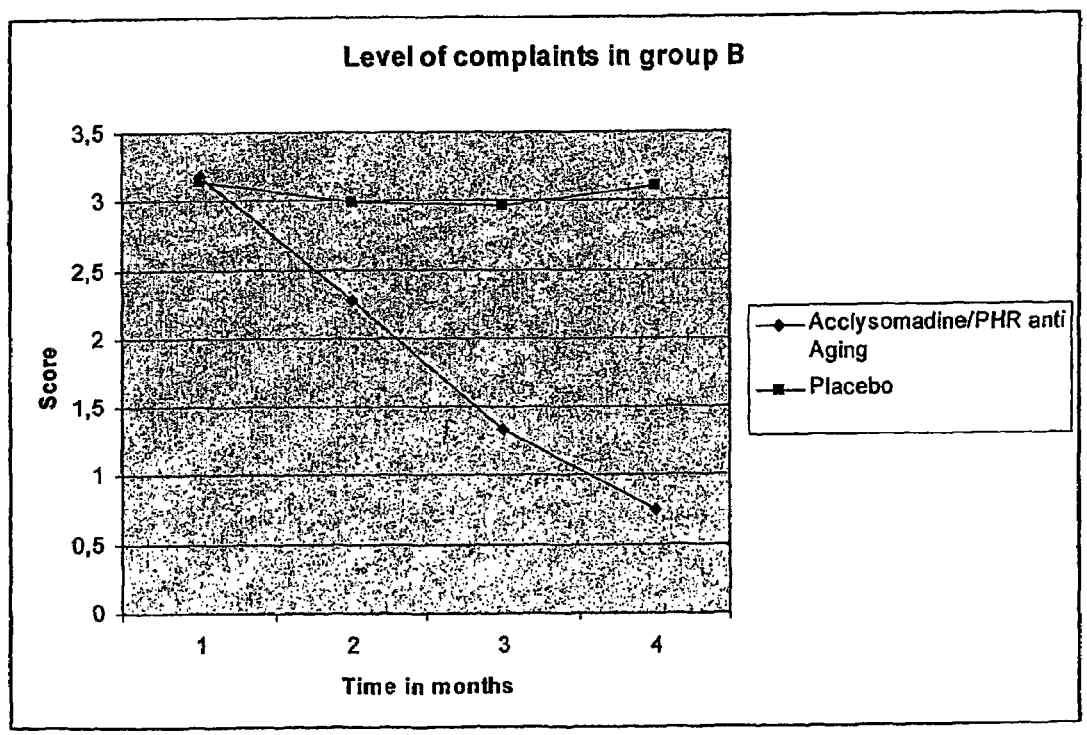
Figure 6C:
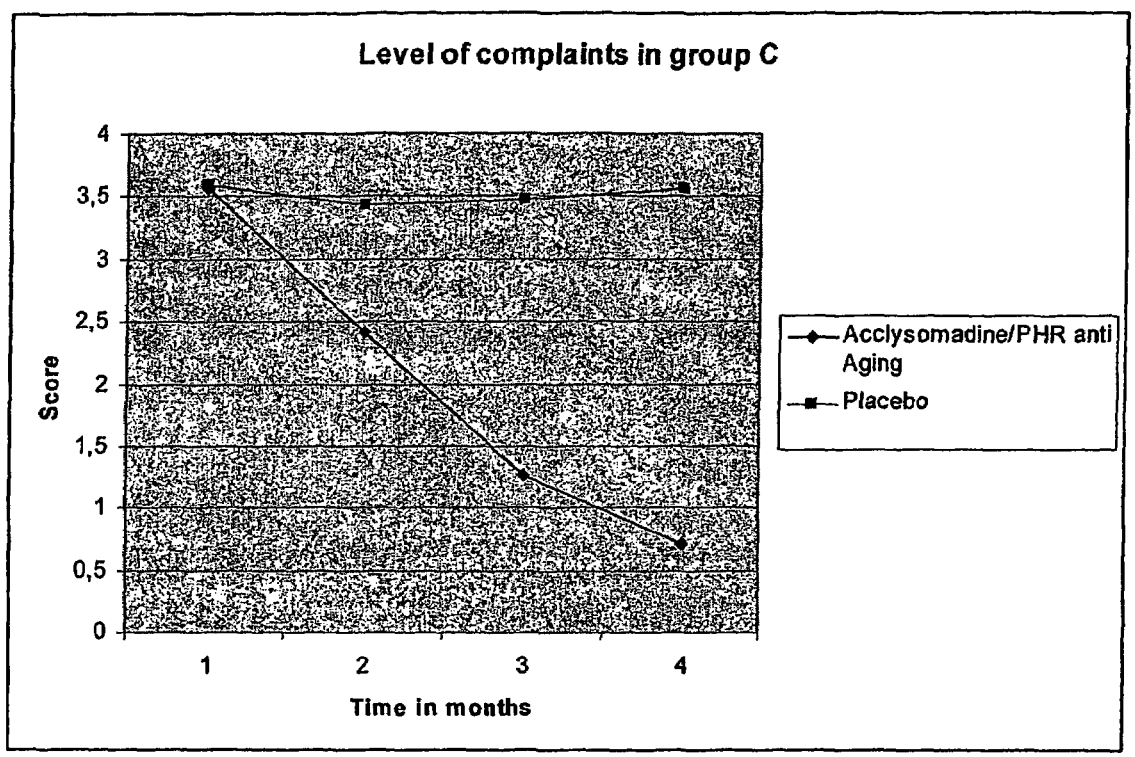

FIG. 6A-C: Levels of complaints in individuals with general anti-aging problems during medication with a composition of the invention.

Figure 7A:
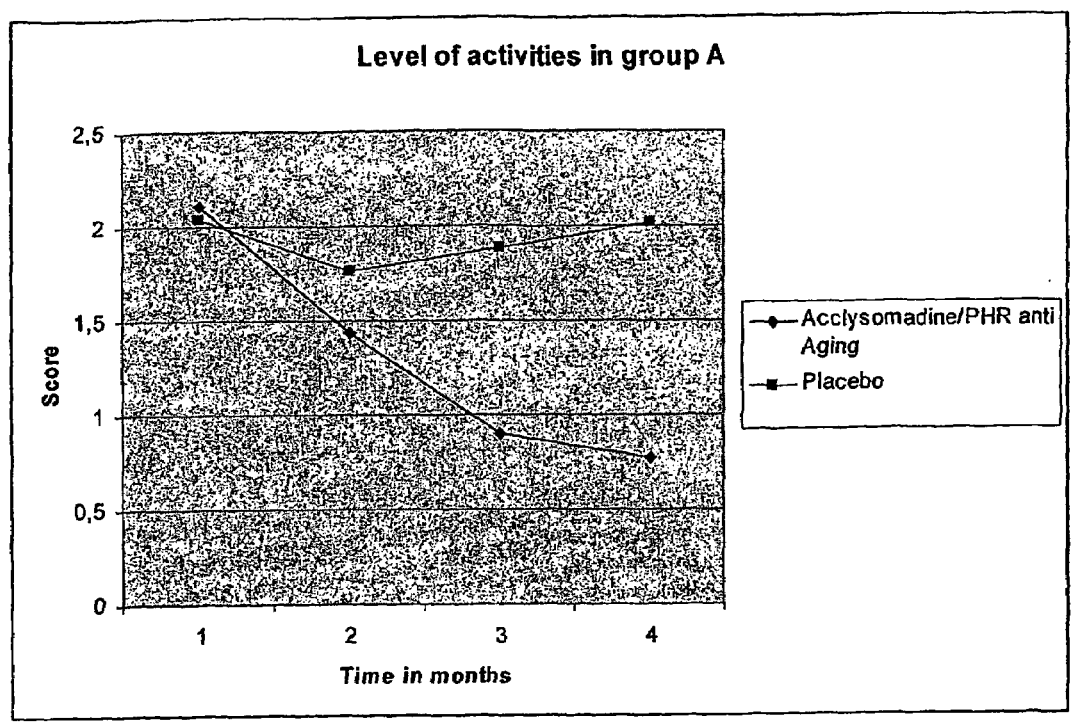
Figure 7B:
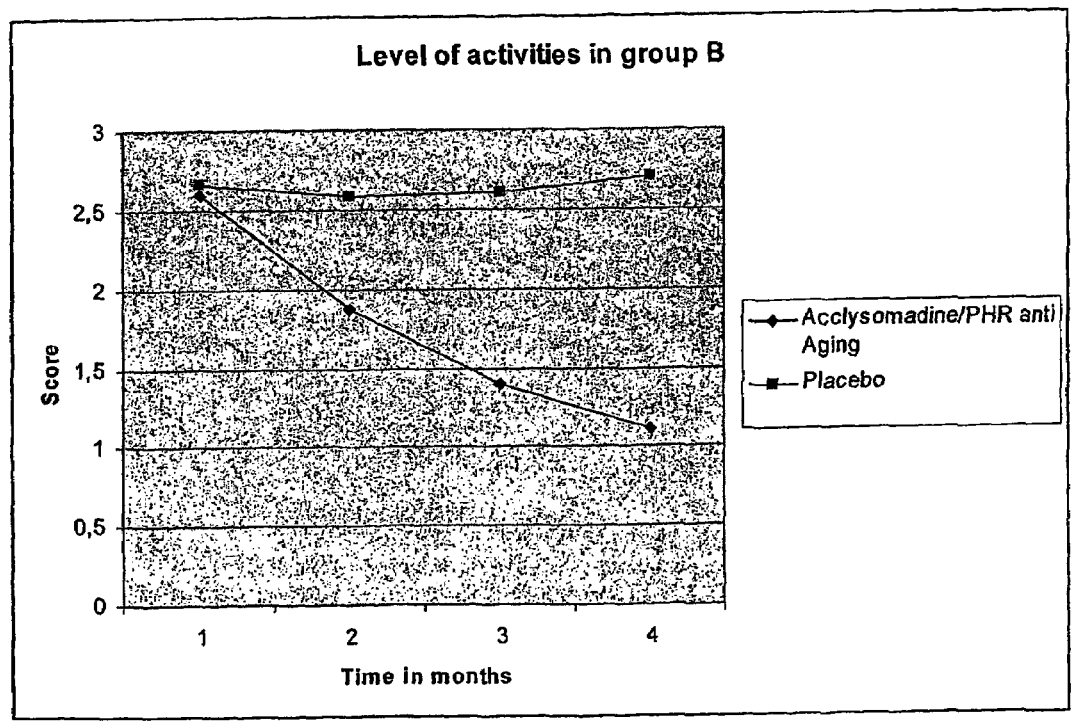
Figure 7C:
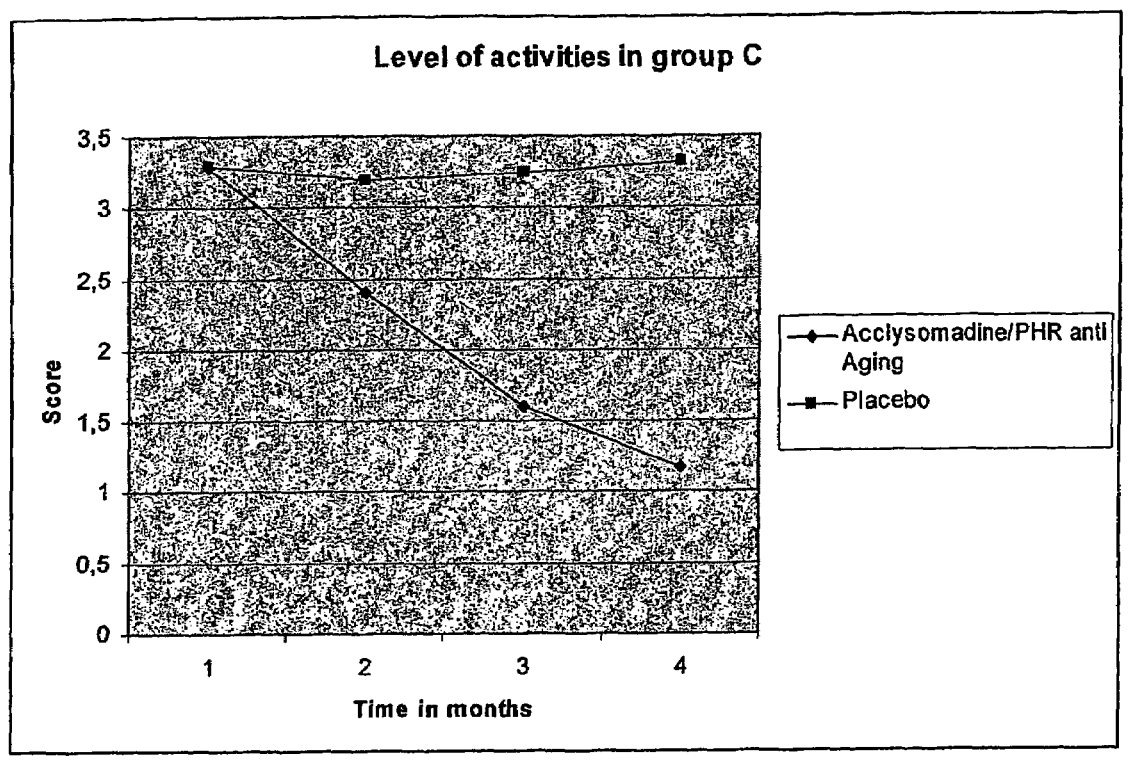

FIG. 7A-C: Levels of activity in individuals with general anti-aging problems during medication with a composition of the invention.

Figure 8:
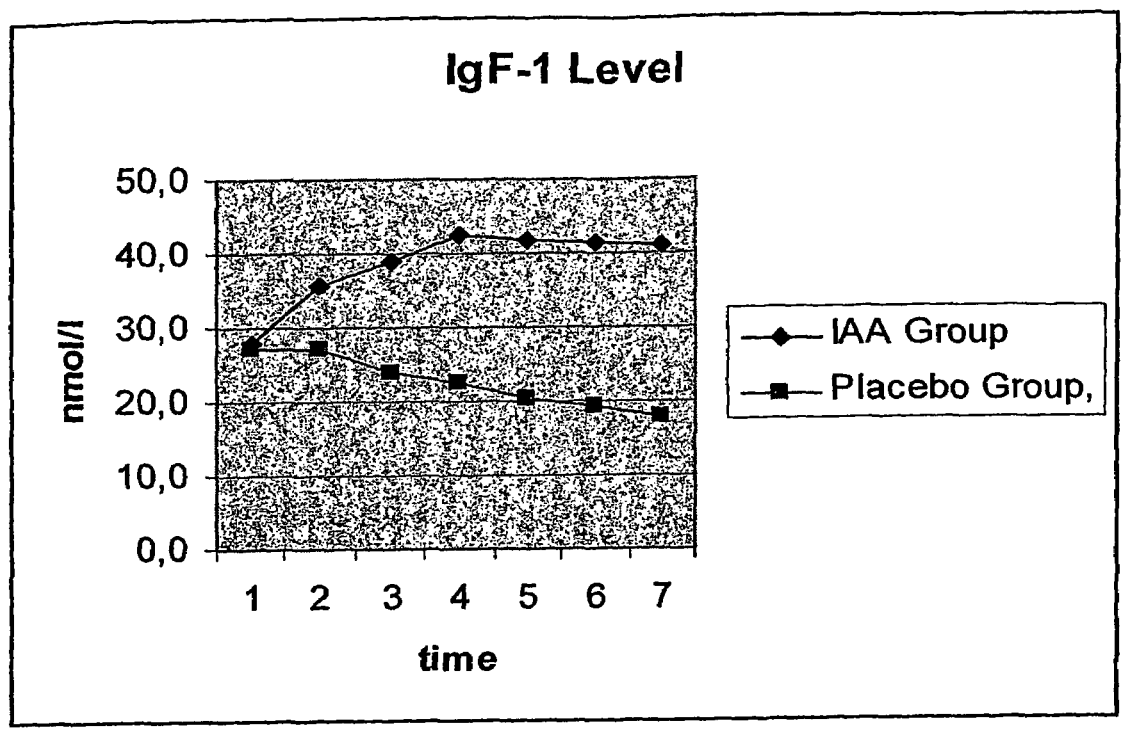

FIG. 8: IGF-1 level in athletes taking IAA or a placebo.

EXAMPLES

Example 1

Use of the Composition of the Invention in the Treatment of Chronic Fatigue Syndrome 1. Introduction The chronic fatigue syndrome (CFS) is clinically defined by feelings of fatigue, that exist for longer than 6 months, in the absence of a proper medical diagnosis. In CFS patients the symptomatology is very wide and consists of neuro-cognitive problems, muscle pains, multiple joints pains, headache, non-refreshing sleep, post-exertional malaise, adenopathy and sore throat. Because of the relatively high prevalence (117/100.000 adults in the Netherlands) and unavailability of a successful treatment the conditions are a burden to society both with respect to medical care and the economy. This example gives the effects of the composition of the invention on the course of CFS. The supplement has auxin as the active ingredient and increases the plasma IGF-1 concentration 2. Material en Methods Eight women varying in age from 25 to 53 year having severe complaints of fatigue that made it impossible to function normally both at work and in free time. All reported an excessive need for sleep, which was never refreshing even though it was prolonged (more than 12 hours). After excluding all other diseases and infections they were all diagnosed for CFS. Physical examination did not reveal any abnormalities in heart and lungs.

Blood samples of 20 ml were taken and liver and kidney functions, the red and white hemogram, IGF-1 en IGF-BP3 determined. The patients took 1000 mg/day (corresponding to 40 mg IAA and 960 mg salt and WPC 70) of the composition of the invention for 4 weeks. After this the dosage was reduced by 250 mg (corresponding to 10 mg IAA) every 2 weeks to 750 mg/day, 500 mg/day 250 mg/day respectively.

Check-ups were performed and blood samples taken (for determining IGF-1 and IGF-BP3) after 1, 3 and 5-7 months of therapy.

At the start of the study and at each check-up point, the work participation and physical activity pattern were scored on a scale from 1 to 10 and plotted as the percentage of the patient's normal activities. Hormone assays for IGF-1 were performed by means of an immuno-assay Assay (DSL-5600 ACTIVE™, DSL Deutschland GmbH, Germany) having an intra-assay variance of 3.0% and an inter-assay variance of 4.9%. IGF-BP3 was determined by means of an immuno-assay Assay (DSL-5600 ACTIVE™, DSL Deutschland GmbH, Duitsland) having an intra-assay variance of 4.4% and an inter-assay variance of 6.6%.

3. Statistics

All values are presented as mean±SD. The Wilcoxon signed rank test for paired observations was applied to show differences between hormone values on each point of time. In case a p value<0.05 was found, the differences were considered to be significant.

4. Results

All patients had very severe restrictions resulting in a high non-attendance at work. The participation in work and the physical activity level of all 8 women was very low before the treatment. Only 2 patients worked 1 or 1.5 day/week. Normal activities like climbing stairs and going for a walk were considered to be impossible or a heavy burden. However, already after 1 month of treatment 5 of 8 women worked for 1 or more days, while all stated that their capacity to perform normal physical work was highly increased.

After 5 month of therapy, the participation in work was increased to 69.4% (50-100%), while the placebo group was the same as at the start of the study.

The plasma IGF-1 level (FIG. 1) of the patients was at the first visit in only three patients higher than the standard value of 20 μg/l. The plasma IGF-1 values increased significantly after 1 months of treatment with the composition of the invention (p<0.001), a trend that persisted after 3 months of treatment (p<0.01), after which the values did not significantly increase.

The plasma IGF-BP3 value (FIG. 1) decreased significantly in time. This means that the free IGF-1 was increased.

5. Discussion

The composition of the invention appears to positively influence the course of the CFS. This is accompanied by a significant increase in plasma IGF-1 level and a decrease in the major binding protein, IGF-BP3. This means that the free IGF-1 concentration (biologically active fraction) in blood is increased.

Example 2

Double Blind Study with a Group of 20 Patients

The next study had a double blind, placebo controlled design. 20 Subjects known with CFS were included and treated either with the composition (10 mg IAA, 100 mg NaCl, 140 mg WPC 70) of the invention, for 3 months, or with a placebo. After this period, 54% of the subjects receiving the composition of the invention improved in mood state as indicated by an adapted profile of mood state (POMS) questionnaire, against 15% of the placebo group. IGF-1 values increased with 40% in the treated group, and remained essential unchanged in the placebo group.

Example 3

A Double-Blind, Placebo-Controlled Study of the Composition of the Invention with Amino Acids in Patients with Chronic Fatigue Syndrome Ninety individuals suffering from CFS (according to the Holmes and/or Fukuda definition) entered the study. They were not allowed to take any other medication than minor pain relievers and homeopathic medication. At baseline, week 4 and week 8 IGF-1, IGF-BP3 and safety parameters, such as liver tests and haematology, were determined. The treatment protocol consisted of 4 weeks 250 mg composition (10 mg IAA, 100 mg NaCl and 140 mg WPC 70) of the invention four times a day in combination with the amino acid preparation All-Amino S (Optipharm) (Table 3-1) and subsequently 4 weeks 250 mg of the composition of the invention twice a day in combination with the amino acid preparation. The primary efficacy variable was the change from baseline in CFS as measured by the Clinician's Global Impression Scale (CGI) after 4 and 8 weeks of treatment.

TABLE 3-1

Composition of All-Amino S

| Amino acid | mg per capsule | mg/gr powder |
|---|---|---|
| L-Lysine HCl | 50 | 43.2 |
| L-Histidine base | 30 | 25.9 |
| L-Arginine base | 125 | 108 |
| L-Asparagine mono | 74 | 63.9 |
| L-threonine | 41 | 35.4 |
| L-Serine | 53 | 45.8 |
| L-Proline | 110 | 95 |
| L-Alanine | 34 | 29.4 |
| L-Cystine | 9.4 | 8.1 |
| L-Valine | 71.5 | 61.7 |
| L-Methionine | 32 | 27.6 |
| L-Isoleucine | 59 | 50.9 |
| L-Tyrosine | 16 | 13.8 |
| L-Leucine | 102 | 88.2 |
| L-Phenylalanine | 22 | 19 |
| L-Tryptophane | 13 | 11.2 |
| L-Cysteine mono | 10 | 8.6 |
| L-Glutamine | 15.3 | 13.2 |
| L-Taurine | 10.7 | 9.2 |
| L-Glutamic acid | 230 | 199 |
| L-Carnithine | 50 | 43.2 |

In the test group the IGF-1 levels increased significantly at week 4 and week 8 compared to the placebo group ($p<0.0002$). In the test group 54% noted an improvement in the symptoms, compared to 16% in the placebo group. The symptom change according to the CGI yielded an improvement in the group receiving the composition of the invention at week 4 ($p<0.004$) and at week 8 ($p<0.0003$). No significant changes were noted in the placebo group.

The composition of the invention in combination with amino acids give an improvement in CFS symptoms. No major adverse effects were noted.

Example 4

Use of the Composition of the Invention in Type 2 Diabetes Patients

1. Introduction

The system of IGF-I and its binding proteins is a complex system with many physiological functions including metabolic regulations. This example aimed to describe changes of its particular components in type 2 diabetic patients. Clinical examination and estimation of serum concentrations of IGF-I and IGF-BP3 influenced by supplementation with IAA were performed. A relationship has been proven between glycaemic control and serum IGF-I levels, with worse control being associated with lower IGF-I levels.

2. Material and Methods

The Patients

5 Male patients type 2 diabetic subjects took part in the study. They were all very difficult to regulate. When the study started, the average HbA1c was to be approx. 9.0%. The patients had no other clinical problems. Also the IgF-BP3/IgF-1 ratio had to be over 10. The age of the subjects were between 45 years and 75 years with an average of 58. The period of the investigation was 6 months. At the start of the study, after 2 month, 4 months and at the end at 6 months, blood was taken. The following parameters were checked; IGF-1 and IGF-PB-3. At the start also safety parameters (liver tests, haematology) were determined. Every 8 weeks, HbA1c was determined. The HbA1c test is a lab test which reveals average blood glucose over a period of two to three months.

All samples from one subject were analysed in the same run to avoid intra-assay variability. Quantification of IGF-1 was performed using an immunoradiometric assay (IRMA) (DSL-5600 ACTIVE™, DSL, Germany GmbH, Germany). Intra- and inter-assay variance was: 4.0% and 9.2% and 1.5% for IGF-1. The Hba1c was analysed on HPLC Menarine HA 81-60.

Calculations and Statistics

The total work output of every subject was calculated with a 2-way ANOVA for repeated measures and the hormone values were analysed with the Wilcoxon test. In all cases a p value of $<0.05$ was accepted as significant.

Medication with IAA

1 Capsule IAA contained 10 mg IAA, 100 mg NaCl, and 140 mg WPC 70

| Month 1 and 2 | | |
|---|---|---|
| IAA | in the morning | 1 mg (1 capsule) |
| | in the afternoon | 1 mg (1 capsule) |
| | In the evening | 1 mg (1 capsule) |
| Month 3 and 4 | | |
| IAA | in the morning | 1 mg (1 capsule) |
| | in the evening | 1 mg (1 capsule) |
| Month 5 and 6 | | |
| IAA | in the morning | 1 mg (1 capsule) |

3. Results

With all subjects, the average IgF-1 level increased from 10.8 nmol/l to 14.1 after 6 months (Table 4-1). All subjects started with a ration above 10. At the start the average was 10.6. After 6 months, the ratio was 6.8 (Table 4-2). The HbA1c decreased from 9.0 to 6.7% (Table 4-3).

TABLE 4-1

| IgF-1 level in nmol/l | | | | | | | |
|---|---|---|---|---|---|---|---|
| | Month 0 | Month 1 | Month 2 | Month 3 | Month 4 | Month 5 | Month 6 |
| Subject 1 | 11.1 | 12.5 | 13.1 | 13.8 | 14.3 | 14.9 | 15.2 |
| Subject 2 | 9.6 | 10.1 | 10.6 | 11.1 | 11.8 | 12.1 | 12.9 |
| Subject 3 | 10.4 | 10.8 | 11.6 | 12.1 | 12.6 | 13.3 | 13.9 |
| Subject 4 | 11..2 | 11.6 | 11.9 | 12.3 | 12.8 | 13.3 | 14.4 |
| Subject 5 | 11.3 | 12.0 | 12.6 | 13.0 | 13.5 | 13.9 | 14.3 |
| Average | 10.7 | 11.4 | 12.0 | 12.5 | 13.0 | 13.5 | 14.1 |

TABLE 4-2

| Ratio IgF-BP3/IgF-1 | | | | | | | |
|---|---|---|---|---|---|---|---|
| | Month 0 | Month 1 | Month 2 | Month 3 | Month 4 | Month 5 | Month 6 |
| Subject 1 | 10.2 | 9.7 | 9.0 | 8.6 | 8.0 | 7.2 | 6.6 |
| Subject 2 | 10.6 | 10.1 | 8.6 | 8.3 | 7.6 | 6.8 | 6.3 |
| Subject 3 | 10.8 | 9.9 | 9.4 | 8.9 | 8.3 | 7.6 | 7.2 |
| Subject 4 | 11.3 | 10.8 | 9.2 | 8.8 | 7.8 | 7.3 | 6.9 |
| Subject 5 | 10.0 | 8.9 | 8.5 | 8.1 | 7.6 | 7.2 | 6.9 |
| Average | 10.6 | 9.9 | 8.9 | 8.5 | 7.9 | 7.2 | 6.8 |

TABLE 4-3

| HbA1c | | | | |
|---|---|---|---|---|
| | Week 0 | Week 8 | Week 16 | Week 24 |
| Subject 1 | 9.6 | 8.9 | 8.0 | 7.4 |
| Subject 2 | 9.0 | 8.2 | 7.1 | 6.4 |
| Subject 3 | 9.1 | 8.3 | 7.4 | 6.6 |
| Subject 4 | 8.6 | 7.6 | 6.9 | 6.3 |
| Subject 5 | 8.8 | 8.3 | 7.6 | 6.8 |
| Average | 9.0 | 8.3 | 7.4 | 6.7 |

4. Discussion

The patients felt better after the treatment.

Example 5

Use of the Invention for the Treatment of Individuals With General Aging Problems 1. Methods 180 Individuals suffering from fatigue, depression, concentration problems, stress (burn-out) and bad shape entered the study. Other medication was excluded from the research. The period of the treatment is 6 months. They were not allowed to take any other medication. At baseline, at the start, after 1 month, 2 months and 3 months, IGF-1, IGF-BP3 and safety parameters (liver tests, haematology) were determined. Every month, the IgF-1 and the IgF-BP3 were checked. The treatment protocol consisted of 3 months 1 sachet (75 mg acclydin, corresponding to 3.75 mg IAA) of the preparation of the invention either in the morning or in the evening.

Composition of an Anti-Aging Sachet According to the Present Invention.

| Vitamins | |
|---|---|
| vitamin A | 1.833 I.E. |
| β-carotene | 2.333 I.E. |
| vitamin B1 (thiamine) | 16.6 mg |
| vitamin B2 (riboflavin) | 12.5 mg |
| vitamin B6 | 12.5 mg |
| vitamin B12 | 15 µg |

-continued

| | |
|---|---|
| vitamin C | 600 mg |
| vitamin E (D-α-tocopherol) | 58.3 mg |
| vitamin D3 | 31 I.E. |
| folic acid | 125 µg |
| niacin | 25 mg |
| niacinamid | 25 mg |
| vitamin B5 (panthothene acid) | 75 mg |
| biotin | 50 µg |
| bioflavonioc complex | 16.6 mg |
| PABA | 8.3 mg |
| inositol | 12.5 mg |
| choline | 25 mg |
| Minerals | |
| magnesiumoxide | 33.3 mg |
| potassium | 16.6 mg |
| Trace elements | |
| chromium | 33.3 µg |
| zinc | 8.3 mg |
| Iodine | 25 µg |
| Manganese | 1.6 mg |
| selenium | 33.3 µg |
| molybdenum | 16.6 µg |
| boron | 330 µg |
| Amino acids | |
| L-cysteine | 33.3 mg |
| DL-methionine | 11.6 mg |
| glutamine | 500 mg |
| betaine | 30 mg |
| Remaining | |
| pinecone nut extract | 20 mg |
| grape nut extract | 80 mg |
| acclydine (3.75 mg IAA, 30 mg NaCl, 41.25 mg WPC 70) | 75 mg |

The primary efficacy variable was the change from baseline in CFS as measured by the questionnaire (activities and complaints, see Annexes 1 and 2) and the IGF-1 and IGF-BP3 values.

The individuals were divided in the following groups:

| A | 30-45 Years | 30 Sachets of the invention 30 Placebo | |
|---|---|---|---|
| | Test group A | Male 14 | Female 16 |
| | Placebo group A | Male 12 | Female 18 |
| B | 46-60 Years | 30 sachets of the invention 30 Placebo | |
| | Test group B | Male 17 | Female 13 |
| | Placebo group B | Male 15 | Female 15 |
| C | >61 Years | 30 sachets of the invention 30 Placebo | |
| | Test group C | Male 14 | Female 16 |
| | Placebo group C | Male 16 | Female 14 |

Before the study started, all individuals filled out the questionnaire (Annexes 1 and 2). This was repeated every month when blood was also taken. The questionnaire is divided in two parts (called herein "part 1" and "part 2").

Part 1 gives an insight into the development of which complaints occur and how serious they were over a period of 3 months. This part had a scale of 0 to 4.

Part 2 gives an insight into the development of activities which were performed over a period of 3 months. This part had a scale of 0 to 4.

Explanation Scale Part 1.
4. The individual had serious/major complaints
3. The individual had considerable complaints
2. The individual had moderate complaints
1. The individual had little complaints
0: The individual had no complaints at all Explanation Scale Part 2.
4: The individual performed almost no activities
3: The individual performed little activities
2: The individual performed moderate activities
1: The individual performed considerable activities
0: The individual can perform all activities he/she wants 2. Materials All samples from one subject were analysed in the same run to avoid intra-assay variability. GH was assayed with a chemiluminescence kit (Nichols Institute Diagnostics, San Juan Capistrano, Calif., USA). Quantification of IGF-1 and IGF-BP3 was performed using an immunoradiometric assay (IRMA) (DSL-5600 ACTIVE™, DSL, Germany GmbH, Germany). Intra- and inter-assay variance was: 4.0% and 9.2% for GH; 3.0% and 1.5% for IGF-1 and 4.4% and 6.6% for IGF-BP3.

Calculation and Statistics

The total work output of every subject was calculated with a 2-way ANOVA for repeated measures and the hormone values were analysed with the Wilcoxon test. In all cases a p value of <0.05 was accepted as significant.

3. Results

IgF-1 Concentrations
Group A

In the group that was given the composition of the invention the IgF-1 level increased statistically significant over a period of 3 months with ca. 19% (Table 5-1). At point 0 (start of the study) the level had an average value of 25.1 nmol/l. At point 3 (end of the study) the IgF-1 level had an average of 29.9 nmol/l.

The level of IgF-1 in the placebo group shows no significant difference. At point 0 (start of the study) the level had an average value of 26.0 nmol/l. At point 3 (end of the study) the IgF-1 level had an average of 25.9 nmol/l.

Group B

In the group that was given the composition of the invention the IgF-1 level increased statistically significant over a period of 3 months with ca. 24% (Table 5-1). At point 0 the level had an average value of 20.6 nmol/l. At point 3 the IgF-1 level had an average of 25.6 nmol/l.

The level of IgF-1 in the placebo group shows no significant difference. At point 0 the level had an average value of 19.9 nmol/l. At point 3 the IgF-1 level had an average of 20.4 nmol/l.

Group C

In the group that received the composition of the invention the IgF-1 level increased statistically significant over a period of 3 months with ca. 35% (Table 5-1). At point 0 the level had an average value of 14.9 nmol/l. At point 3 the IgF-1 level had an average of 20.3 nmol/l.

The level of IgF-1 in the placebo group shows no significant difference. At point 0 the level had an average value of 14.5 nmol/l. At point 3 the IgF-1 level had an average of 14.4 nmol/l.

TABLE 5-1

| | IgF-1 Level in nmol/l | | | |
|---|---|---|---|---|
| | Time in months | | | |
| | 0 | 1 | 2 | 3 |
| Group A | | | | |
| Average Test group | 25.1 | 28 | 29.4 | 29.9 |
| SD Test group | 3.44 | 3.12 | 3.22 | 3.08 |
| Average placebo group | 26 | 27.1 | 25.4 | 25.9 |
| SD placebo group | 3.6 | 3.42 | 3.32 | 3.51 |
| Group B | | | | |
| Average Test group | 20.6 | 24.1 | 25 | 25.6 |
| SD Test group | 3.03 | 3.29 | 3.1 | 3.21 |
| Average placebo group | 19.9 | 20.7 | 19.2 | 20.4 |
| SD placebo group | 2.99 | 3.4 | 3.22 | 3.25 |
| Group C | | | | |
| Average Test group | 14.9 | 17.9 | 19.4 | 20.3 |
| SD Test group | 1.94 | 2.14 | 1.88 | 2.38 |
| Average placebo group | 14.5 | 14 | 15.1 | 14.4 |
| SD placebo group | 1.96 | 1.67 | 2.02 | 1.97 |

Complaints
Group A

In the group that was given the composition of the invention the complaints decreased statistically significant over a period of 3 months (Table 5-2). At point 0 the level had an average value of 2.88. At point 3 it had an average of 0.62.

The level the complaints in the placebo group showed no significant difference. At point 0 the level had an average value of 2.90. At point 3 it had an average of 2.79.

Group B

In the group that received the composition of the invention the complaints decreased statistically significant over a period of 3 months (Table 5-2). At point 0 the level had an average value of 3.18. At point 3 it had an average of 0.75.

The level the complaints in the placebo group showed no significant difference. At point 0 the level had an average value of 3.15. At point 3 it had an average of 3.10.

Group C

In the group that was given the composition of the invention the complaints decreased statistically significant over a period of 3 months (Table 5-2). At point 0 the level had an average value of 3.56. At point 3 it had an average of 0.72.

The level of the complaints in the placebo group showed no significant difference. At point 0 the level had an average value of 3.60. At point 3 it had an average of 3.56.

TABLE 5-2

|  | Month 0 | Month 1 | Month 2 | Month 3 |
|---|---|---|---|---|
| Group A | | | | |
| Average Test group | 2.88 | 2.02 | 1.11 | 0.62 |
| SD Test group | 0.31 | 0.26 | 0.21 | 0.15 |
| Average Placebo group | 2.9 | 2.69 | 2.88 | 2.79 |
| SD Placebo group | 0.31 | 0.24 | 0.29 | 0.32 |
| Group B | | | | |
| Average Test group | 3.18 | 2.28 | 1.34 | 0.75 |
| SD Test group | 0.32 | 0.25 | 0.23 | 0.12 |
| Average Placebo group | 3.15 | 2.99 | 2.97 | 3.1 |
| SD Placebo group | 0.3 | 0.28 | 0.34 | 0.31 |
| Group C | | | | |
| Average Test group | 3.56 | 2.41 | 1.27 | 0.72 |
| SD Test group | 0.27 | 0.22 | 0.25 | 0.2 |
| Average Placebo group | 3.6 | 3.44 | 3.48 | 3.56 |
| SD Placebo group | 0.3 | 0.24 | 0.29 | 0.31 |

Activities

Group A

In the group that received the composition of the invention the activities decreased statistically significant over a period of 3 months (Table 5-3). At point 0 the level had an average value of 2.11. At point 3 it had an average of 0.77.

The level of the activities in the placebo group showed no significant difference. At point 0 the level had an average value of 2.04. At point 3 it had an average of 2.02.

Group B

In the group that received the composition of invention the activities decreased statistically significant over a period of 3 months (Table 5-3). At point 0 the level had an average value of 2.60. At point 3 it had an average of 1.11.

The level of the activities in the placebo group showed no significant difference. At point 0 the level had an average value of 2.66. At point 3 it had an average value of 2.70.

Group C

In the group that was given the composition of the invention the activities decreased statistically significant over a period of 3 months (Table 5-3). At point 0 the level had an average value of 3.28. At point 3 it had an average of 1.17.

The level of the activities in the placebo group showed no difference. At point 0 the level had an average value of 3.30. At point 3 it had an average of 3.32.

TABLE 5-3

|  | Month 0 | Month 1 | Month 2 | Month 3 |
|---|---|---|---|---|
| Group A | | | | |
| Average Test group | 2.11 | 1.44 | 0.9 | 0.77 |
| SD Test group | 0.28 | 0.33 | 0.29 | 0.3 |
| Average Placebo group | 2.04 | 1.76 | 1.88 | 2.02 |
| SD Placebo group | 0.29 | 0.3 | 0.27 | 0.29 |
| Group B | | | | |
| Average Test group | 2.6 | 1.88 | 1.4 | 1.11 |
| SD Test group | 0.44 | 0.4 | 0.45 | 0.44 |
| Average Placebo group | 2.66 | 2.59 | 2.61 | 2.7 |
| SD Placebo group | 0.4 | 0.44 | 0.41 | 0.45 |
| Group C | | | | |
| Average Test group | 3.28 | 2.4 | 1.6 | 1.17 |
| SD Test group | 0.6 | 0.69 | 0.63 | 0.65 |
| Average Placebo group | 3.3 | 3.2 | 3.25 | 3.32 |
| SD Placebo group | 0.67 | 0.54 | 0.6 | 0.65 |

4. Discussion

The purpose of this Example was to investigate whether the composition of the invention could increase work output. The results show that the composition has an ergogenic effect. It does not increase physical performance acutely, but enhances the ability to perform repeated bouts of strenuous exercise. The placebo groups show no significant changes in performance and the psychical condition. The composition of the invention gives an improvement on all symptoms. The individuals of the groups who use the composition have more energy and feel better. Also it can be concluded from the questionnaire that the test group feels younger, more optimistic, not depressed and happier.

Example 6

Food Supplement for Athletes

1. Introduction

This example was performed to investigate the influence of IAA on the level of IgF-1 with intensive training. The experiment was performed for 12 weeks.

2. Methods

20 Athletes entered the study. Other medication was excluded from the research. The period of the treatment was 12 weeks. They were not allowed to take any other medication or food supplements. They continued their level of training. After 2 weeks the training was intensified with 25%. At baseline, at the start, after 2 weeks, 4 weeks, 6 weeks, 8 weeks, 10 weeks and after 12 weeks, IGF-1 and safety parameters (liver tests, haematology) were determined. The group was divided into two groups of 10 athletes. Group A received IAA, group B got a placebo.

| Group A | 6 male | 4 female |
|---|---|---|
| Group B | 5 male | 5 female |

All samples from one subject were analysed in the same run to avoid intra-assay variability. GH was assayed with a chemiluminescence kit (Nichols Institute Diagnostics, San Juan Capistrano, Calif., USA). Quantification of IGF-1 was performed using an immunoradiometric assay (IRMA) (DSL-5600 ACTIVE™, DSL, Germany GmbH, Germany). Intra- and inter-assay variance was: 4.0% and 9.2% for GH; 3.0% and 1.5% for IGF-1.

Calculations and Statistics

The total work output of every subject was calculated with a 2-way ANOVA for repeated measures and the hormone values were analysed with the Wilcoxon test. In all cases 1 p value of <0.05 was accepted as significant.

IAA

The following schedule was used for the supplements. 1 IAA capsule contained 10 mg IAA, 100 mg NaCl, 140 mg WPC 70. 1 Glutamine capsule contained 500 mg glutamine. The Amino Acids that were taken are as described in Table 3-1.

| Week 1 and 2 | | |
|---|---|---|
| IAA | in the morning | 8 mg (2 capsules) |
|  | In the evening | 8 mg (2 capsules) |
| Amino Acids | in the morning | 5200 mg (6 capsules) |
|  | In the evening | 5200 mg (6 capsules) |
| Glutamine | in the morning | 500 mg (1 capsule) |
|  | In the evening | 500 mg (1 capsule) |
| Week 3 until 12 | | |
| IAA | in the morning | 4 mg (1 capsule) |
|  | In the evening | 4 mg (1 capsule) |
| Amino Acids | in the morning | 2700 mg (3 capsules) |
|  | In the evening | 2700 mg (3 capsules) |
| Glutamin | in the morning | 500 mg (1 capsule) |
|  | In the evening | 500 mg (1 capsule) |

3. Results

In group A, who were given IAA, the IgF-1 level increased statistically significant over a period of 8 weeks with ca. 47.7% (Table 6-1). At point 0 (start of the study) the level had an average value of 27.9 nmol/l. At the end of the study the IgF-1 level had an average of 41.2 nmol/l.

In group B, who were given placebo, the level of IgF-1 shows a decrease. At point 0 (start of the study) the level had an average value of 27.3 nmol/l. At the end of the study the IgF-1 level had an average of 17.8 nmol/l.

TABLE 6-1

| IgF-1 Level in nmol/l | | | | | | | |
|---|---|---|---|---|---|---|---|
|  | 0 | 1 | 2 | 3 | 4 | 5 | 6 |
| Group A | | | | | | | |
| Average Test group | 27.9 | 35.8 | 38.9 | 42.5 | 41.7 | 41.4 | 41.2 |
| SD Test group | 3.41 | 3.45 | 3.34 | 3.51 | 3.44 | 3.48 | 3.44 |
| Group B | | | | | | | |
| Average placebo group | 27.3 | 27.1 | 24.1 | 22.6 | 20.5 | 19.2 | 17.8 |
| SD placebo group | 3.42 | 3.51 | 3.47 | 3.43 | 3.45 | 3.39 | 3.24 |

4. Conclusions

The group that received IAA, in the end performed better, they were more alert and focused. For the placebo group, the performances decreased over 12 weeks. The intensive training caused fatigue with this group whereas the active group was still fit. IAA seams to be an effective product to increase the performance of athletes.

Example 7

Treatment of Poor Growing Piglets with IAA

1. Introduction

This Example is for testing the theory of the impaired functioning of the hypothalamic-pituitary-adrenal (HPA) axis by infection pressure and the influence of the treatment on health and growth.

The trial was done in a well managed farm with 1000 sows of the Dutch Landrace. Although the farm is well run, the technical performance is not optimal. There were latent problems with mortality and with growth rates of the piglets. There are too many poor growing piglets, without fully understanding the technical or veterinary reason. There is no clear pathology to be seen on the farm.

2. Methods

The farmer selected the poor growing piglets for this weaning period. The piglets were weaned for two days at the start of the trial. There were 3 groups: the normal well growing piglets which serve as a control group, the B group with 78 poor growers that are treated with 12.5 mg/kg/LW (Life Weight) IAA and the X group with 52 poor growers that are not treated.

Blood samples for IGF-1 measuring were taken from each group at the beginning of the trial and at the end of the trial. Two pens (13 piglets) of the B and X group, were weighed at the beginning and at the end of the trial. The active ingredient IAA was mixed in dextrose. This mixture was added 5 grams per piglet per day to the feed, which resulted in a dosage of 12.5 mg/kg/LW. The B group received the treatment five days after the first IGF-1 measuring.

3. Results

Two days after weaning, there is no difference in IGF-1 levels between the 3 groups. IGF-1 levels are low, due to the stress of weaning. But already after one week the farmer notices a clear difference between the group B and group X. The piglets in group B are looking better, the bellies were better filled and the general appearance of the piglets started to look better than in group X.

This phenomenon gets more obvious as the treatment continues. There are less poor growers in the B group, skin and hair is looking much better, less medical treatment is needed in group B.

TABLE 7-1

| IGF-1 levels in nmol/L | | |
|---|---|---|
|  | IGF-1 measurement | |
|  | $1^{st}$ | $2^{nd}$ |
| Control group | | |
| 1 | 0.8 | 14 |
| 2 | 4.3 | 16.6 |
| 3 | 7.9 | 25.4 |
| 4 | 6.1 | 30.3 |
| 5 | 3.9 | 31.7 |
| total | 23 | 118 |
| average | 4.6 | 23.6 |
| Treated group B | | |
| 1 | 3 | 25.2 |
| 2 | 2.7 | 28.9 |

TABLE 7-1-continued

IGF-1 levels in nmol/L

|  | IGF-1 measurement | |
|---|---|---|
|  | 1st | 2nd |
| 3 | 6.1 | 25.5 |
| 4 | 5.3 | 29.9 |
| 5 | 5.7 | 16.9 |
| total | 22.8 | 126.4 |
| average | 4.56 | 25.28 |
| Non-treated group X | | |
| 1 | 2.9 | 11.3 |
| 2 | 4.3 | 21.6 |
| 3 | 1.6 | died |
| 4 | 13.1 | 20.8 |
| 5 | 1.3 | 15.1 |
| total | 23.2 | 68.8 |
| average | 4.64 | 17.2 |

After 21 days of treatment IGF-1 levels were measured again. The B group was on the level of the healthy control group (25.3 vs. 23.6 nmol/l) but was clearly higher than the non-treated group X (17.2 nmol/l).

TABLE 7-2

Weight gain

| Pen nr. | Weighing 1 | | Weighing 2 | | av. Weight gain |
|---|---|---|---|---|---|
|  | Total (kg) | average | Total (kg) | average |  |
| B 3L | 86 (n = 13) | 6.62 | 150 (n = 11) | 13.64 | 7.02 |
| B 3R | 88 (n = 13) | 6.77 | 167 (n = 13) | 12.85 | 6.08 |
| X 4L | 80 (n = 12) | 6.67 | 141 (n = 11) | 12.82 | 6.15 |
| X 4R | 92 (n = 13) | 7.08 | 171 (n = 13) | 13.15 | 6.08 |

Pen B 3L(eft) grew on average 850 grams more then their neighbours from pen X 4 L(eft). Pen B 3 R(ight) gained on average as much weight as their neighbours from pen X 4R(ight), but weighed 310 grams less at the start of the trial. On average, the treated group gained (for the pens that were weighed) almost 0.5 kg more over a period of 21 days.

After the treatment is stopped, the piglets from group B continue to perform better than group X.

Poor growing piglets start to look and grow better than the non-treated group. These characteristics are clearly coupled with a higher IGF-1 level in the treated groups. The results of this trial confirm that treatment for 14-21 days with 12.5 mg/kg/LW IAA effectively restores IGF-1 levels in poor growing piglets. There is enough evidence to believe that once this level is restored to normal, these piglets will catch up the lost growth and will do well during the fattening period, without continuing the treatment.

Example 8

Treatment of Crowing Laying Hens with IAA

1. Introduction

Following the successful treatment of poor growing piglets in Example 6, the same treatment was tested on poor growing laying hens, since this is a big problem in rearing laying hens. The flocks do not grow uniformly, and about 10-15% of the birds have a too poor growing performance. The same logic as for the poor growing piglets (infections raise the cytokine levels and lower the IGF-1, see also Example 8) can be applied to rearing laying hens.

2. Methods

Growing laying hens of 10 weeks old were selected in the flock to create four groups of ten hens:

Group GB: 10 normally growing hens, not treated

Group GNA: 10 normally growing hens, treated with 10 mg/kg/LW IAA (LW=live weight)

Group SB: 10 poorly growing hens, not treated

Group SNA: 10 poorly growing hens, treated with 10 mg/kg/LW IAA

In this example, not only the poor growing birds were treated, but also normally growing animals. The birds receive daily forced oral treatment with a capsule which contains IAA. The different groups are weighed every week. Treatment is continued at least until the hens start laying, to see if the if the period of onset of laying is influenced by the treatment.

3. Results

From the first week on a better weight gain is seen in both the treated groups. The difference in weight gain is consistent over the first four weeks of the trial. The group GNA has now about 2 weeks advance over the normal rearing schedule and the SNA group has caught back up to schedule. The last couple of weeks of the experiment were very stressful for the birds, since it was very hot, and the birds were vaccinated against ILT.

TABLE 8-1

| Group no. | weight | weight gain | weight | weight gain |
|---|---|---|---|---|
|  | GB | | GNA | |
| 1 | 690.5 |  | 740 |  |
| 2 | 802 | 111.5 | 883 | 143 |
| 3 | 878 | 76 | 996 | 113 |
| 4 | 995 | 117 | 1095 | 99 |
| 5 | 1098 | 103 | 1222 | 127 |
| total weight gain | 407.5 |  | 482 |  |
|  | SB | | SNA | |
| 1 | 498.5 |  | 489.5 |  |
| 2 | 585 | 86.5 | 598 | 108.5 |
| 3 | 685 | 100 | 718 | 120 |
| 4 | 790 | 105 | 885 | 167 |
| 5 | 907 | 117 | 995 | 110 |
| total weight gain | 408.5 |  | 505.5 |  |

The weight gain already after one week gave a clear indication that IAA has the same effect as seen in piglets and calves. Therefore it is assumed that the mode of action is the same in chicken as in mammals. The group SNA shows the highest weight gain in this test period. So there seems to be a phenomenon of catching up of "lost" growth, after the IAA has normalized the function of the HPA-axis.

It can also be concluded that IAA has an action in "normal" birds, and that the IAA does not seem to induce a resistance to it's mode of action at the dosage of 10 mg/kg/LW.

So the results of this example indicate that the use of IAA can bring poor growing hens back to the normal rearing schedule and prevent loss of animals for normal production, can speed up the rearing process and deliver much stronger birds at the end of the rearing period

Example 9

Treatment of Survivors of Porcine Reproductive and Respiratory Syndrome Virus with IAA 1. Introduction From experience with treatment of humans with Chronic Fatigue Syndrome (CFS) it follows that efficacy of the treatment is closely linked to the restoration of normal IGF-1 serum levels. Growth rates in most animals, including pigs, are also correlated with IGF-1 status. It is known that IGF-1-concentrations are affected by disease and immunological challenge. Some of the piglets surviving PRRSV infections show resembling symptoms to patients with CFS (no drive to move nor to eat, looking sad etc.).

Therefore IGF-1-concentrations were tested in PRRSV piglets and they were treated with IAA.

2. Methods

The experiment was performed with Belgian Land Race piglets that had a history of PRRSV. The piglets were weaned at four weeks and relocated per twelve piglets per pen. IGF-1 levels from three different groups were tested at the age of five weeks.

Group P

These are the pigs with the big problems. They are looking poor, have a low weight, bad colour and some of them have *Staphylococcus* infections. It was the firm belief of the farmer and the veterinarian that these piglets would not reach the end of the fattening cycle. Blood samples were taken at random from five of the twelve piglets.

| Ref. | IGF-1 nmol/l |
|---|---|
| Piglet 1 | 2.3 |
| Piglet 2 | <0.5 |
| Piglet 3 | <0.5 |
| Piglet 4 | 2.0 |
| Piglet 5 | 1.8 |

The results indicate a severe affection of the IGF-1 levels and a clear correlation between poor growth and health and IGF-1 concentration.

Group R

These piglets were looking the best. They received a special pre-starter feed before weaning. The IGF-1 concentration of five piglets was checked at random.

| Ref. | IGF-1 nmol/l |
|---|---|
| Piglet 1 | 4.3 |
| Piglet 2 | 1.0 |
| Piglet 3 | 7.3 |
| Piglet 4 | 22.2 |
| Piglet 5 | 14.7 |

The special pre-starter seems to boost the IGF-1 levels in this group.

Group T

These were normal looking piglets. They received a regular piglet starter feed before weaning

| Ref. | IGF-1 nmol/l |
|---|---|
| Piglet 1 | 2.7 |
| Piglet 2 | <0.5 |
| Piglet 3 | 0.8 |
| Piglet 4 | 0.5 |
| Piglet 5 | 3.5 |

These piglets have normal growth, but less good then the R group. This also reflects in the lower IGF-1 levels.

3. Treatment

After seeing the low IGF-1 levels in group P, it was decided to give them the same treatment as in humans with CFS. The average weight of the piglets would have been around seven kilos at five weeks of age. They were treated with 125 mg of the composition comprising 5 mg IAA and 120 mg NaCl and WPC 70 for ten days. The product was fed in a through, mixed in liquid feed. All the piglets ate from the same through.

4. Results

After ten days of treatment, at random blood samples were taken from the different groups. A code was added for the size of the animals (K=small; N=normal; Z=heavy).

Group P

All twelve pigs were still alive and their condition had dramatically improved. They all had a nice pink color, no more stiff hair, all the ears were in normal position, no piglets suffered from *Staphylococcus* infection anymore. They had gained very much in weight and in muscle growth and had caught up very much to the average of the rest of the "normal" litter mates. All external signals for good health were now present.

At random IGF-1 concentrations of five piglets of this group were measured

| Ref. | IGF-1 nmol/l |
|---|---|
| Piglet PN | 0.8 |
| Piglet PK | <0.5 |
| Piglet PZ | 4.2 |
| Piglet PK | <0.5 |
| Piglet PN | <0.5 |

The IGF-1 levels do not reflect the dramatic improvement in health, weight and condition of the piglets. The IGF-1 levels did not rise. The same is seen in CFS patients. The patient feels much better after a couple of weeks of treatment, but there is no increase yet in IGF-1 concentration. This increase in IGF-1 occurs only a couple of weeks later. We assume that all the extra IGF-1 production is used in the process of the extra-growth. Still there is a clear link between individual weight and IGF-1 levels.

Group R

These piglets are now on a normal commercial piglet starter diet, so no longer on pre-starter formula. This group is growing normally. No particular signs are present. Blood samples were taken at random from six piglets.

| Ref. | IGF-1 nmol/l |
|---|---|
| Piglet RK | 11.4 |
| Piglet RN | 11.4 |
| Piglet RN | 32.6 |
| Piglet RZ | 18.7 |
| Piglet RK | 9.8 |
| Piglet RZ | 10.4 |

The average IGF-1 concentration rose in two weeks from 9.9 nmol/l to 15.72.

Group T

These piglets continue to be on their original piglet starter feed. This group is also growing normally without any particular symptoms. Five blood samples were taken at random for the IGF-1 concentration.

| Ref. | IGF-1 nmol/l |
| --- | --- |
| Piglet TZ | 10.5 |
| Piglet TN | 6.0 |
| Piglet TN | 3.1 |
| Piglet TN | 10.9 |
| Piglet TZ | 16.3 |

The average IGF-1 concentration rose in two weeks from 1.6 to 9.36 nmol.

Another three weeks later blood samples were again taken, but only from the problem group.

| Ref. | IGF-1 nmol/l |
| --- | --- |
| Piglet 1 | 30.0 |
| Piglet 2 | 23.4 |
| Piglet 3 | 65.1 |
| Piglet 4 | 13.7 |
| Piglet 5 | 60.1 |
| Piglet 6 | 36.9 |
| Piglet 7 | 55.6 |

These results show clearly that the piglet's IGF-1 production was increased, even though the treatment was stopped.

5. Discussion

The treatment with IAA improved dramatically the condition of the Problem piglets. Their immune system eliminated the *Staphylococcus* infections. This improvement is not immediately reflected in the IGF-1 serum concentration, but three weeks after the treatment was stopped, the IGF-1 level had risen to what is believed almost normal levels.

It is known that multiple infections raise TNF-alfa, IL-1 and IL-6 six to much higher levels then single infections. It is also known that in severe infections TNF-alfa, IL-1 and IL-6 modulate reactions that prevent the transformation of GH into IGF-1. This leads to high serum concentrations of GH and low serum concentrations of IGF-1. These high levels of GH will give a feed back reaction to the HPA-axis to produce less GH-RH. For some animals, as for human CFS patients, after the source of infection is gone, the HPA axis stays in a "sleeping mode", induced by the feed back of the high GH-levels. IAA provides the necessary stimulus to put the HPA-axis again in the "active mode", and to restore normal IGF-1 levels, which in their turn lead to a normally functioning immune system and a normal growth, or for CFS patients normal levels of energy.

The invention claimed is:

1. A method of treating decreased ability for muscular exercise in a subject suffering from chronic fatigue syndrome, the method comprising:
   administering to the subject a compound comprising indole acetic acid (IAA), 4-hydroxy-IAA, 4-methoxy-IAA, 5-hydroxy-IAA, 5-methoxy-IAA, 6-hydroxy-IAA, 6-methoxy-IAA, 7-hydroxy-IAA or 7-methoxy-IAA.

2. The method according to claim 1, further comprising administering to the subject at least one amino acid.

3. The method according to claim 1, wherein the compound is an active ingredient in a composition, and the composition comprises 1 to 100 mg of the compound.

4. The method according to claim 1, wherein the compound is administered in a capsule.

5. The method according to claim 3, wherein the composition comprises 10 to 90 mg of the compound.

6. The method according to claim 5, wherein the composition comprises 40 mg of the compound.

* * * * *